US012788937B2

(12) United States Patent
Berent et al.

(10) Patent No.: US 12,788,937 B2
(45) Date of Patent: Nov. 10, 2026

(54) ADAPTIVE AUDITORY STIMULATION SYSTEM FOR ENHANCING SLOW-WAVE SLEEP USING REAL-TIME EEG FEEDBACK

(71) Applicant: NextSense, Inc., Mountain View, CA (US)

(72) Inventors: Jonathan Berent, Mountain View, CA (US); Malcolm Slaney, Mountain View, CA (US)

(73) Assignee: NextSense, Inc., Mountain View, CA (US)

( * ) Notice: Subject to any disclaimer, the term of this patent is extended or adjusted under 35 U.S.C. 154(b) by 0 days.

(21) Appl. No.: 19/426,397

(22) Filed: Dec. 19, 2025

(65) Prior Publication Data

US 2026/0115409 A1 Apr. 30, 2026

Related U.S. Application Data

(60) Provisional application No. 63/736,958, filed on Dec. 20, 2024.

(51) Int. Cl.
*A61M 21/00* (2006.01)
*G06F 3/01* (2006.01)
*H04R 1/10* (2026.01)

(52) U.S. Cl.
CPC ............. *A61M 21/00* (2013.01); *G06F 3/015* (2013.01); *H04R 1/1016* (2013.01); *H04R 1/1041* (2013.01); *A61M 2021/0027* (2013.01)

(58) Field of Classification Search
CPC ........... A61M 21/00; A61M 2021/0027; G06F 3/015; H04R 1/1016; H04R 1/1041
USPC ...................................................... 600/26–28
See application file for complete search history.

(56) References Cited

U.S. PATENT DOCUMENTS

2015/0343168 A1* 12/2015 Garcia Molina ..... A61M 21/02 600/26
2016/0082222 A1* 3/2016 Garcia Molina ..... A61M 21/02 600/27
2017/0000970 A1* 1/2017 Garcia Molina ...... A61B 5/369
2019/0143073 A1* 5/2019 Grossman .............. A61B 5/374 600/28
2019/0298967 A1* 10/2019 Garcia Molina ..... A61M 21/02
2019/0344042 A1* 11/2019 Garcia Molina ..... A61M 21/02
2020/0086078 A1* 3/2020 Poltorak ................ A61N 2/006

(Continued)

*Primary Examiner* — Sunita Reddy
(74) *Attorney, Agent, or Firm* — Shumaker, Loop & Kendrick, LLP

(57) ABSTRACT

The present disclosure provides a method for enhancing slow-wave sleep through adaptive auditory stimulation. The method comprises receiving electroencephalogram (EEG) signals from an earbud device worn by a user during sleep, and detecting neural activity patterns indicative of deep sleep. The method comprises causing the earbud device to deliver an auditory stimulus with current parameters, and applying correlation analysis to determine correlation between neural features from the EEG signals and an audio parameter matrix. The method comprises determining an attention metric from the correlation, wherein the attention metric quantifies neural entrainment with auditory stimuli. Responsive to the attention metric falling below a threshold, the method modifies the current auditory stimulus parameters and causes delivery of subsequent auditory stimulus using modified parameters, thereby enhancing slow-wave oscillations during sleep.

28 Claims, 6 Drawing Sheets

(56) References Cited

U.S. PATENT DOCUMENTS

| | | | | |
|---|---|---|---|---|
| 2020/0368491 | A1* | 11/2020 | Poltorak .............. | A61N 1/0456 |
| 2021/0170138 | A1* | 6/2021 | Garcia Molina .... | A61B 5/7267 |
| 2022/0054797 | A1* | 2/2022 | Van Den Ende ..... | A61M 21/02 |
| 2022/0218941 | A1* | 7/2022 | Vu ......................... | A61B 5/397 |
| 2023/0218855 | A1* | 7/2023 | Hemmsen .............. | A61B 7/023<br>600/28 |
| 2023/0371872 | A1* | 11/2023 | Harpaz ................ | A61B 5/7267 |
| 2023/0404466 | A1* | 12/2023 | Poltorak ................ | A61B 5/374 |

* cited by examiner

ADAPTIVE AUDITORY STIMULATION SYSTEM FOR ENHANCING SLOW-WAVE SLEEP USING REAL-TIME EEG FEEDBACK

PRIORITY INFORMATION

This application claims priority to U.S. Provisional Patent Application No. 63/736,958, titled "ADAPTIVE AUDITORY STIMULATION SYSTEM FOR ENHANCING SLOW-WAVE SLEEP USING REAL-TIME EEG FEEDBACK," filed Dec. 20, 2024.

FIELD OF INVENTION

The present disclosure relates to sleep enhancement technologies, and more particularly to a system and method for optimizing slow-wave sleep through adaptive auditory stimulation using real-time electroencephalogram (EEG) feedback.

BACKGROUND

Sleep enhancement systems face a fundamental technical challenge in providing real-time adaptive auditory stimulation that synchronizes with a user's neural oscillations during slow-wave sleep. During slow-wave sleep, the brain exhibits characteristic delta-frequency oscillations (0.5-4 Hz) that are associated with memory consolidation and restorative processes. However, these neural patterns vary significantly between individuals and change dynamically throughout sleep cycles, creating computational challenges for systems attempting to deliver precisely timed auditory interventions. The technical problem lies in processing electroencephalogram (EEG) signals in real-time to extract sleep-related parameters and dynamically adjust auditory stimulus properties to maintain synchronization with the user's changing neural state without causing sleep disruption.

Current solutions for sleep enhancement typically employ fixed auditory stimulation patterns, such as static pink noise or predetermined phase-locked audio bursts delivered at regular intervals. These systems utilize basic sleep stage detection through accelerometry or simple EEG analysis to trigger pre-programmed audio sequences. Some existing approaches apply Canonical Correlation Analysis (CCA) to correlate audio features with EEG signals, but operate with static audio libraries and predetermined correlation thresholds. These systems generally process EEG data in discrete epochs and apply uniform stimulation parameters across all users, without accounting for individual neural response variations or real-time changes in brain state.

The limitations of current approaches create several technical shortcomings that reduce their effectiveness in enhancing slow-wave sleep. Fixed stimulation patterns fail to adapt to the dynamic nature of neural oscillations, resulting in poor temporal alignment between audio stimuli and slow-wave activity. Static correlation thresholds cannot accommodate individual differences in neural response patterns or account for changes in sleep depth throughout the night. Additionally, existing systems lack the computational capability to perform real-time analysis of multiple EEG channels while simultaneously adjusting audio parameters such as frequency, amplitude, and phase in response to detected neural patterns. These technical constraints limit the ability to maintain optimal synchronization between auditory stimulation and slow-wave oscillations, reducing the potential for effective sleep enhancement.

SUMMARY

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

According to an aspect of the present disclosure, a method for enhancing slow-wave sleep through adaptive auditory stimulation is provided. The method comprises receiving, by a processor, electroencephalogram (EEG) signals from an earbud device worn by a user during a sleep period. The method comprises detecting, by the processor, neural activity patterns in the EEG signals indicative of a deep sleep state. The method comprises causing the earbud device to deliver to the user an auditory stimulus having a current set of auditory stimulus parameters. The method comprises applying, by the processor, a correlation analysis algorithm to determine, for a time window associated with the delivered auditory stimulus, a correlation between a neural feature representation extracted from the EEG signals and an audio parameter matrix corresponding to the current set of auditory stimulus parameters. The method comprises determining an attention metric from the correlation, wherein the attention metric quantifies neural entrainment with auditory stimuli delivered to the user. The method comprises, responsive to the attention metric falling below a threshold value for the attention metric, modifying the current set of auditory stimulus parameters to generate modified auditory stimulus parameters, and causing delivery of a subsequent auditory stimulus using the modified auditory stimulus parameters, thereby enhancing slow-wave oscillations in the user's brain during the sleep period.

According to another aspect of the present disclosure, a system for enhancing slow-wave sleep through adaptive auditory stimulation is provided. The system comprises an earbud device wearable by a user and configured to detect electroencephalogram (EEG) signals during a sleep period and to deliver auditory stimuli to the user. The system comprises at least one processor. The system comprises at least one memory storing instructions that, when executed by the at least one processor, cause the system to receive the EEG signals from the earbud device during the sleep period, detect neural activity patterns in the EEG signals indicative of a deep sleep state, cause the earbud device to deliver to the user an auditory stimulus having a current set of auditory stimulus parameters, apply a correlation analysis algorithm to determine, for a time window associated with the delivered auditory stimulus, a correlation between a neural feature representation extracted from the EEG signals and an audio parameter matrix corresponding to the current set of auditory stimulus parameters, determine an attention metric from the correlation, wherein the attention metric quantifies neural entrainment with auditory stimuli delivered to the user, and responsive to the attention metric falling below a threshold value for the attention metric, modify the current set of auditory stimulus parameters to generate modified auditory stimulus parameters, and cause the earbud device to deliver a subsequent auditory stimulus using the modified auditory stimulus parameters, thereby enhancing slow-wave oscillations in the user's brain during the sleep period.

The foregoing general description of the illustrative embodiments and the following detailed description thereof are merely exemplary aspects of the teachings of this disclosure and are not restrictive.

BRIEF DESCRIPTION OF FIGURES

Non-limiting and non-exhaustive examples are described with reference to the following figures.

DETAILED DESCRIPTION

Figure 1:
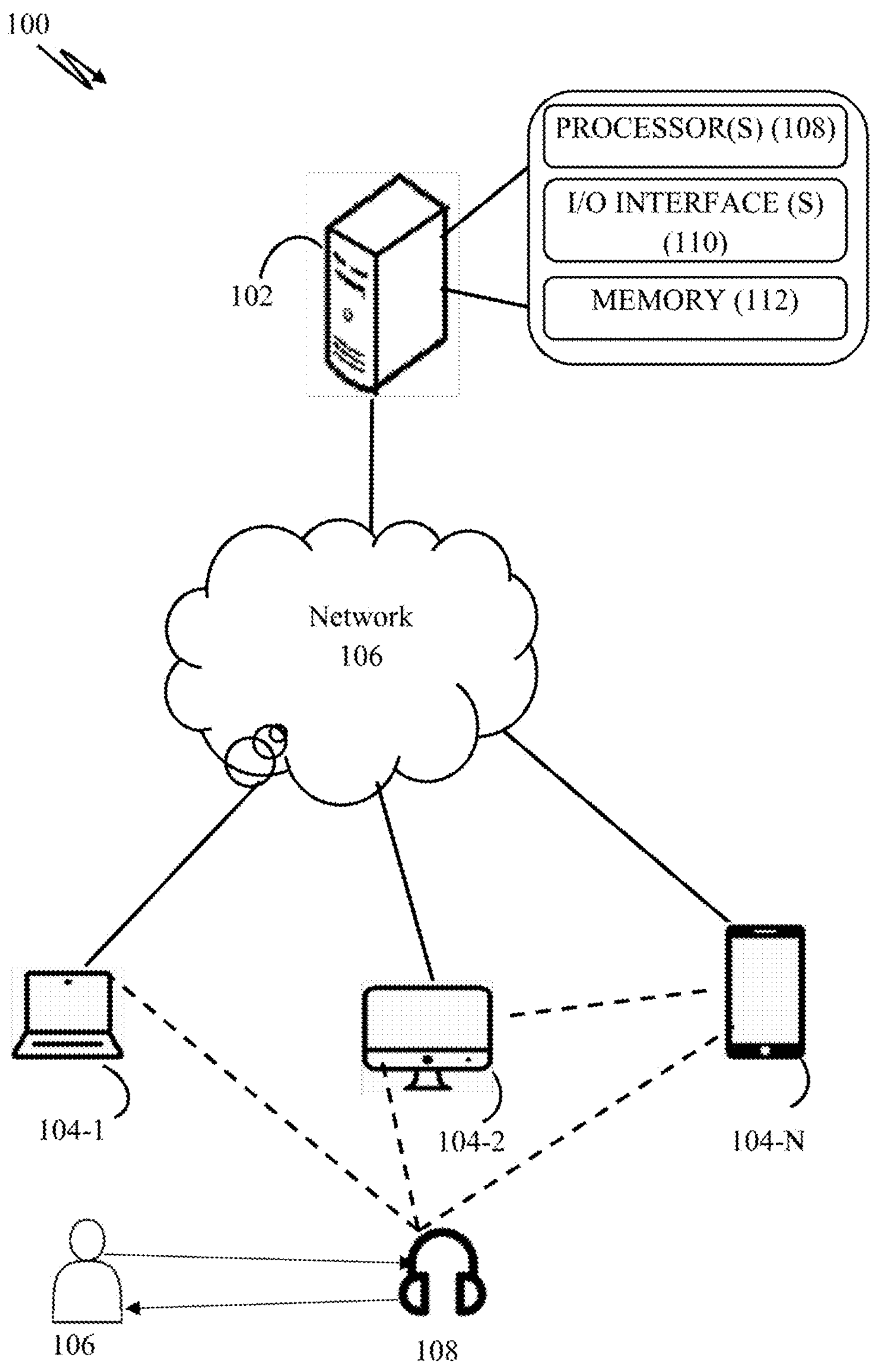
FIG. 1 illustrates a network implementation of a system for enhancing slow-wave sleep through adaptive auditory stimulation, according to aspects of the present disclosure.

The following description sets forth exemplary aspects of the present disclosure. It should be recognized, however, that such description is not intended as a limitation on the scope of the present disclosure. Rather, the description also encompasses combinations and modifications to those exemplary aspects described herein.

In various embodiments, the present disclosure relates to systems and methods for enhancing slow-wave sleep (SWS) by using an earbud device to deliver adaptive auditory stimulation during a user's sleep period. The earbud device may include EEG sensing electrodes and audio transducers, enabling simultaneous acquisition of brain activity and delivery of controlled auditory stimuli. A processor receives EEG signals during sleep, detects neural activity patterns indicative of a deep sleep state, and initiates delivery of an auditory stimulus configured using a current set of auditory stimulus parameters.

Conventional sleep-audio approaches typically rely on fixed stimulation profiles (e.g., preset tones or volume levels) or coarse sleep-stage detection, which can lead to suboptimal entrainment, reduced efficacy across users, and potential sleep disruption when stimulation is mistimed or poorly tuned. The disclosed embodiments address these technical problems by dynamically quantifying, in a time-locked manner, how the user's brain responds to the delivered auditory stimulus. In particular, rather than assuming a uniform response, the system evaluates the user-specific neural response during a time window associated with the stimulus and uses that response to control subsequent stimulation.

To accomplish this, in some embodiments the processor applies a correlation analysis algorithm to determine a correlation between (i) a neural feature representation extracted from the EEG signals and (ii) an audio parameter matrix corresponding to the current set of auditory stimulus parameters. From the correlation, the processor determines an attention metric that quantifies neural entrainment with the delivered auditory stimuli (e.g., a measure of how strongly the EEG features track, phase-lock to, or otherwise correlate with stimulus parameter variations). When the attention metric falls below a threshold, the processor modifies one or more auditory stimulus parameters (e.g., stimulus timing, intensity, spectral shaping, modulation characteristics, or binaural/spatial parameters) to generate modified auditory stimulus parameters and causes delivery of a subsequent auditory stimulus using the modified parameters.

Accordingly, the disclosed embodiments provide a closed-loop, user-adaptive stimulation technique that improves the technical field of sleep enhancement by enabling individualized and time-resolved adjustment of auditory stimulation based on measured neural entrainment, thereby promoting enhanced slow-wave oscillations while reducing the likelihood of ineffective or disruptive stimulation. In the detailed description, example implementations are provided for (a) EEG acquisition and pre-processing on or in communication with an earbud device, (b) deep sleep detection logic and time-window selection, (c) neural feature extraction and formation of the neural feature representation, (d) construction of the audio parameter matrix from stimulus configuration and/or time-varying stimulus attributes, (e) correlation analysis and computation of the attention metric, and (f) parameter-update rules, thresholds, and safety constraints used to generate modified auditory stimulus parameters for subsequent stimuli.

The system includes an earbud device configured to (i) sense EEG signals from the user during a sleep period and (ii) deliver auditory stimuli to the user, and a processor configured to detect deep sleep state from the EEG signals and adapt auditory stimulation based on measured neural entrainment. In some embodiments, one or more electrodes are positioned in the ear canal and/or concha to acquire EEG signals during sleep, with the placement selected to maintain contact during typical sleep movement and to provide EEG signals usable for sleep-stage detection and slow-wave activity analysis.

The earbud device further includes one or more acoustic transducers configured to output auditory stimuli (e.g., pink noise, tones, and/or amplitude-modulated waveforms) according to controllable stimulus parameters such as level, timing, spectral shaping, and modulation characteristics. In some embodiments, the earbud device performs front-end signal conditioning of the EEG signals (e.g., amplification, analog-to-digital conversion, and filtering) and transmits the conditioned EEG data via a wireless link to the processor for correlation analysis and closed-loop adjustment of subsequent auditory stimuli.

The system may include one or more processors configured to receive EEG signals acquired by an ear-worn device (e.g., an in-ear and/or near-ear earbud device) during a sleep period and to analyze the EEG signals for sleep-state detection and closed-loop control of auditory stimulation. The processor(s) may be implemented on a user device (e.g., a smartphone), in a dedicated sleep device, and/or in a distributed arrangement in which some operations are performed locally and others are performed remotely. A memory subsystem stores EEG samples and/or derived features and program instructions, and a communication interface conveys the EEG signals (or processed EEG data) from the earbud device to the processor via a wired or wireless link.

In some embodiments, the earbud device includes one or more electrodes positioned at the ear canal and/or concha to acquire EEG signals during sleep, optionally using differential acquisition and/or multiple sensing points to reduce noise and improve robustness to movement. The EEG signals may be sampled at a rate sufficient to detect slow-wave activity and sleep-stage transitions, and may be buffered and segmented into time windows, including time windows associated with delivery of auditory stimuli. The earbud device and/or the processor may perform signal conditioning (e.g., amplification, analog-to-digital conversion, and filtering) to support extraction of a neural feature representation from the EEG signals.

In some embodiments, the processor detects neural activity patterns indicative of a deep sleep state, including patterns associated with slow-wave and/or delta-band activity, and enables, disables, or adjusts auditory stimulation based on the detected state. The processor may further detect conditions under which stimulation is reduced or suppressed, such as micro-arousal signatures, wake/non-deep sleep, or artifact conditions due to motion or electrode displacement. The processor may compute one or more derived measures from the EEG signals (e.g., bandpower and/or slow-oscillation measures) for use in correlation analysis and in determining an attention metric that quantifies neural entrainment with delivered auditory stimuli.

In some embodiments, the processor detects neural activity patterns indicative of a deep sleep state (e.g., slow-wave sleep) by analyzing the EEG signals for slow-wave characteristics, including increased delta-band activity and associated amplitude features. The processor may evaluate EEG content in a delta band (e.g., approximately 0.5-4 Hz) and compute one or more metrics within defined time windows, such as delta-band power, relative delta-band power, slow-wave event rate, slow-oscillation amplitude, and/or related measures. The EEG signals may be segmented into epochs having a predetermined duration and/or processed using a sliding window to continuously update the deep sleep determination during the sleep period.

In some embodiments, the deep sleep determination is based on one or more threshold criteria applied to the computed metrics, where the threshold criteria may be fixed or adaptively determined based on user-specific baseline characteristics, historical data, and/or signal-quality indicators (e.g., electrode impedance or noise level). Where multiple EEG sensing channels are available, the processor may require consistency across channels and may suppress or defer classification when an artifact condition is detected. The processor may further require the deep sleep criteria to be satisfied for at least a minimum duration and/or across multiple consecutive epochs and may apply temporal smoothing to reduce rapid switching between sleep-stage classifications. In some embodiments, the processor detects transitions into and/or out of deep sleep to control initiation, continuation, reduction, or termination of auditory stimulation, and may optionally incorporate negative criteria indicating arousal or lighter sleep as additional gating signals.

The detection criteria for identifying deep sleep may include specific thresholds for both the prevalence and amplitude of delta wave activity within defined time windows. In some cases and not by way of any limitation, the system may determine that deep sleep has been achieved when delta waves comprise at least 20% of a 30-second epoch, indicating that slow-wave activity has become the dominant neural pattern during that time period. This percentage threshold may serve as a quantitative measure of the transition from lighter sleep stages to the deeper, more restorative phases of sleep.

Amplitude analysis may constitute another component of the deep sleep detection process, with the system configured to identify delta waves that exceed specific voltage thresholds indicative of robust slow-wave activity. The detection algorithm may look for delta wave amplitudes exceeding 75 microvolts, measured peak-to-peak, as an indicator of the high-amplitude oscillations characteristic of deep sleep. These amplitude criteria may help distinguish genuine slow-wave sleep from periods of reduced neural activity that may not represent the fully developed deep sleep state.

The epoch-based analysis approach may involve segmenting the continuous EEG signal into discrete time windows, for example and not by way of any limitation—30 seconds in duration, to enable systematic evaluation of sleep stage characteristics over manageable time intervals. Each epoch may be analyzed, in real-time, independently to determine the percentage of time occupied by delta wave activity and the amplitude distribution of detected slow waves. The system may maintain a sliding window analysis to provide continuous assessment of sleep depth while accommodating the natural variability in neural oscillations that occurs during sleep.

Spectral analysis techniques may be employed to quantify the power distribution across different frequency bands within each epoch, enabling precise measurement of delta wave prevalence relative to other neural oscillations. The system may compute power spectral density estimates using methods such as, but not limited to, Fast Fourier Transform (FFT) or Welch's method to determine the relative contribution of delta band activity to the overall EEG signal. This spectral approach may provide a robust foundation for quantifying the 20% threshold criterion for delta wave presence.

The detection algorithm may incorporate adaptive thresholding mechanisms to account for individual variations in baseline EEG characteristics and electrode impedance that may affect signal amplitude measurements. The system may establish personalized amplitude thresholds during initial calibration periods or may adjust detection criteria based on the user's historical sleep data to improve the accuracy of deep sleep identification across different nights and changing physiological conditions.

Multi-channel analysis may enhance the reliability of deep sleep detection by evaluating delta wave characteristics across multiple EEG sensing locations within the earbud device configuration. The system may require consistent delta wave patterns across multiple channels to confirm the presence of deep sleep, reducing the likelihood of false positive detections due to localized artifacts or electrode-specific issues.

The determination that the user has entered slow-wave sleep may be based on sustained detection of the delta wave criteria over multiple consecutive epochs, ensuring that the identified deep sleep state represents a stable neural condition rather than a transient fluctuation in brain activity. The system may implement temporal smoothing algorithms to prevent rapid switching between sleep stage classifications due to brief variations in delta wave characteristics.

Once a deep sleep state is detected, the processor causes the earbud device to initiate delivery of an auditory stimulus configured to enhance slow-wave activity while reducing a likelihood of arousal. The auditory stimulus may include, for example, pink-noise bursts, tones, and/or rhythmic or amplitude-modulated patterns. The auditory stimulus is delivered according to a current set of auditory stimulus parameters, which may include one or more of stimulus onset time(s), inter-stimulus interval, burst duration, intensity, spectral shaping, modulation rate/depth, tempo, phase, waveform shape, and/or channel-specific parameters for left/right output.

The processor controls timing of auditory stimulus delivery relative to a slow-wave component of the EEG signals, including aligning a stimulus onset to occur within a predetermined phase window of a delta-band (e.g., 0.5-4 Hz) oscillation. The auditory stimulus may be generated by digital synthesis and delivered using controlled temporal envelopes (e.g., smooth attack/decay) to reduce abrupt acoustic changes. The auditory stimulus parameters may include an intensity parameter bounded by a maximum intensity threshold to reduce sleep disruption and/or hearing risk, and the processor may reduce, suspend, or terminate stimulation upon detecting a wake state, a non-deep sleep state, a micro-arousal signature, or an artifact condition.

In some embodiments, the system monitors EEG signals during and/or after delivery of an auditory stimulus and evaluates neural response within one or more time windows associated with the stimulus (e.g., overlapping the stimulus interval and/or extending for a response period following stimulus onset). The processor extracts a neural feature representation from the EEG signals for the time window and may compare the features to a pre-stimulus baseline or to features computed during non-stimulated intervals. The neural feature representation may include one or more features indicative of slow-wave sleep and/or entrainment, such as delta-band power in a 0.5-4 Hz band, slow-oscillation phase, slow-oscillation amplitude, slow-wave event rate, dominant slow-wave frequency, and/or cross-frequency coupling measures between delta-band activity and a higher-frequency band.

In some embodiments, the neural feature representation is formed from time-domain, frequency-domain, time-frequency, and/or connectivity-related features computed from one or more EEG channels, and the representation may be organized as a feature vector, a sequence of feature vectors over time, or a matrix/tensor indexed by time, channel, and/or feature type. Additionally or alternatively, the neural feature representation may be generated by a learned feature extractor (e.g., a trained machine-learning model) that maps an EEG segment for the time window to an embedding, which may optionally be normalized and stored for subsequent correlation analysis with a representation of the auditory stimulus.

Further, the processor determines an attention metric that quantifies neural entrainment with auditory stimuli delivered to the user by applying a correlation analysis algorithm to (i) a neural feature representation extracted from the EEG signals for a time window associated with delivery of an auditory stimulus and (ii) an audio parameter matrix corresponding to a current set of auditory stimulus parameters for that time window.

The attention metric may comprise, for example, a phase-locking value, a coherence value, a normalized cross-correlation value, a canonical correlation coefficient, mutual information, a Pearson or Spearman correlation value, and/or a correlation score output by a trained machine-learning model indicative of association between the neural feature representation and the audio parameter matrix.

The processor may compare the attention metric to a threshold value (and optionally apply change detection and/or adaptive thresholding) to determine whether the current stimulus parameters are producing sufficient entrainment.

In some embodiments, the neural feature representation is derived from one or more EEG channels and includes features computed within the time window, such as delta-band power in a 0.5-4 Hz band, slow-oscillation phase, slow-oscillation amplitude, slow-wave event rate, and/or cross-frequency coupling measures between delta-band activity and a higher-frequency band. The neural feature representation may be organized as a feature vector, a sequence of feature vectors over time, or a matrix/tensor indexed by time, channel, and/or feature type. Additionally or alternatively, the neural feature representation may be generated by a learned feature extractor (e.g., a trained model) that maps an EEG segment to an embedding, which may optionally be normalized (including normalization to a bounded range) and stored for subsequent correlation analysis and personalization.

In some embodiments, the auditory stimulus parameters include one or more of stimulus onset time(s), inter-stimulus interval, duration, overall level or gain, frequency or frequency-band limits, spectral shaping, modulation rate and/or depth, temporal envelope parameters (e.g., attack/decay), waveform shape, tempo, and/or binaural/spatial parameters. The processor logs parameter values applied during stimulus delivery and forms an audio parameter matrix for the associated time window. The audio parameter matrix may be structured as a T×P matrix in which rows correspond to time frames within the time window and columns correspond to parameter dimensions, and/or as a time-frequency representation (e.g., a T×F envelope per band), and may include stimulus onset times, an amplitude envelope of the auditory stimulus, and/or a parameter vector including timing and intensity. The audio parameter matrix may optionally be normalized, scaled, or transformed to improve comparability across users and sessions.

In some embodiments, the processor modifies the current set of auditory stimulus parameters when the attention metric indicates insufficient entrainment, including when the attention metric falls below the threshold value, and causes delivery of a subsequent auditory stimulus using modified auditory stimulus parameters. Parameter modification may include adjusting at least one of stimulus frequency, phase and/or onset timing, amplitude and/or intensity, tempo, or waveform shape, including adjusting a stimulus onset time to occur within a predetermined phase window of a 0.5-4 Hz component of the EEG signals. Parameter updates may be bounded to remain within predetermined ranges, including enforcing an intensity parameter bounded by a maximum intensity threshold and constraining timing and/or frequency adjustments to a predetermined range. In some embodiments, the processor incrementally modifies a parameter (e.g., frequency) by a bounded step size and reverses a sign of the step size when a subsequent attention metric decreases relative to a previous attention metric; the processor may also apply hysteresis or other stability logic to reduce rapid switching when the attention metric is near threshold.

In some embodiments, the processor segments the EEG signals into a plurality of epochs having a predetermined duration (optionally overlapping) and forms, for an epoch or for a stimulus-associated time window within the epoch, an EEG data matrix and a corresponding audio parameter matrix. To account for response latency, the processor may evaluate a plurality of candidate lag values defining respective temporal offsets between the EEG data matrix and the audio parameter matrix, align the matrices according to each candidate lag value, and compute a correlation for each alignment.

In an example implementation, the correlation analysis comprises canonical correlation analysis that computes a canonical correlation coefficient between respective projections of the EEG data matrix and the audio parameter matrix, and the attention metric comprises a maximum canonical correlation coefficient across the candidate lag values. The processor may store an optimal lag value associated with the maximum and use the optimal lag value to time-shift a temporal envelope used to control timing of delivery of a subsequent auditory stimulus.

In some embodiments, the processor classifies epochs as stimulated or non-stimulated based on temporal overlap between an epoch and an audio-delivery interval and computes summary statistics for each class, including a mean stimulated attention metric and a mean non-stimulated attention metric. The processor may compute a difference between the means and apply a bootstrap resampling procedure to estimate a confidence interval for the difference. The processor may adjust at least one auditory stimulus parameter when a lower bound of the confidence interval is greater than or equal to a predetermined margin, thereby biasing parameter updates toward changes with statistically supported improvement.

In some embodiments, the processor conditions stimulus delivery and/or parameter modification on sleep continuity and signal quality, including detecting micro-arousal signatures and disabling or reducing auditory stimulation upon detection, and terminating stimulus delivery upon detecting a wake state or a non-deep sleep state. The processor may detect an artifact condition using motion data from an accelerometer of the earbud device (and/or signal-quality indicators) and suppress response assessment and/or suppress parameter modification during the artifact condition. The processor may store EEG-derived features, audio parameter matrices, attention metrics, and selected parameters across sleep periods to support personalization, including selection of initial parameters for subsequent sessions and optional use of predictive models to propose parameter updates.

In some embodiments, the processor applies canonical correlation analysis (CCA) to quantify association between EEG activity and delivered auditory stimulation on an epoch-by-epoch basis. For a given sleep epoch k, the processor forms an EEG data matrix $X_k$ and a stimulus representation matrix $Y_k$, and computes canonical correlation coefficients across a plurality of candidate lag values ($\tau$) to identify an alignment that accounts for latency between stimulus presentation and measurable neural response.

The canonical correlation computation may involve determining linear transformation vectors that maximize the correlation between projections of the EEG data matrix and the auditory stimulus matrix. For each sleep epoch k, the system may compute canonical correlation coefficients $\rho k(\tau)$ where $\tau$ represents the time lag parameter that defines the temporal offset between the neural data and the stimulus representation. The linear projections may be computed by identifying optimal weighting vectors $\alpha$ and $\beta$ that maximize the Pearson correlation between $\alpha^T X_k$ and $\beta^T Y_k(\tau)$, where $X_k$ represents the EEG data matrix for epoch k and $Y_k(\tau)$ represents the time-shifted auditory stimulus matrix.

The time lag analysis may involve evaluating the canonical correlation coefficient across a discrete set of candidate lag values that span a predetermined temporal range designed to capture the various delays that may occur between auditory stimulus presentation and neural response manifestation. The lag range may typically extend from negative values, representing stimulus presentations that precede the neural activity measurements, to positive values, representing stimuli that follow the EEG data acquisition. The temporal range may span several seconds, with lag increments of 50 to 200 milliseconds providing sufficient resolution to identify optimal alignment conditions.

The system may implement time-shifting analysis procedures that systematically align the audio signals with the neural signals across the range of candidate lag values to ensure identification of the temporal offset that produces the highest correlation between the stimulus and response patterns. The time-shifting process may involve temporal interpolation, resampling, or sliding window operations that adjust the relative timing between the EEG data matrix and the auditory stimulus representation while preserving the essential characteristics of both signal types. This temporal alignment capability may be particularly important when employing correlation analysis algorithms other than canonical correlation analysis or when implementing deep neural network approaches that may require precise temporal registration between input and target signals.

For each candidate lag value $\tau$, the system may compute the canonical correlation coefficient by solving the generalized eigenvalue problem that identifies the linear combinations of EEG features and auditory stimulus parameters that exhibit maximum correlation. The computation may involve calculating cross-covariance matrices between the EEG data and the time-shifted stimulus representation, as well as auto-covariance matrices for each data type. The canonical correlation coefficient may be determined as the largest eigenvalue of the matrix equation that relates these covariance structures, providing a normalized measure of the maximum achievable correlation between linear projections of the two data sets.

The attention metric for each sleep epoch k may be defined as the maximum canonical correlation value across all evaluated lag values, expressed mathematically as $a_k = \max_\tau \rho_k(\tau)$. This maximum value may represent the strongest achievable linear relationship between the EEG signals and the auditory stimulus when optimal temporal alignment is employed. The attention metric may provide a quantitative measure of neural entrainment effectiveness that accounts for both the strength of the stimulus-response relationship and the optimal timing conditions under which this relationship is observed.

The system may record the associated optimal lag value $\tau_k = \arg\max_\tau \rho_k(T)$ that corresponds to the temporal offset producing the maximum canonical correlation coefficient for each epoch. The optimal lag value may provide information about the temporal dynamics of neural response to auditory stimulation and may be used to optimize the timing of subsequent stimulus presentations. The recorded lag values may vary across different epochs, users, and stimulus conditions, reflecting individual differences in neural processing delays and the varying effectiveness of different temporal alignment strategies.

The attention metric may be normalized to a bounded focus score that provides a standardized measure suitable for comparison across different epochs, users, and stimulus conditions. The normalization process may employ a linear transformation of the form $f_k = c_1(a_k + c_2)$, where $c_1$ and $c_2$ represent constants selected to map the attention metric values to a predetermined range. The constants may be chosen such that the focus score $f_k$ lies within a bounded interval, such as [0, 1] or [−1, 1], facilitating interpretation and enabling consistent threshold-based decision making across different analysis contexts.

The selection of normalization constants $c_1$ and $c_2$ may be based on statistical analysis of attention metric distributions observed across representative populations or may be determined through calibration procedures that establish appropriate scaling relationships for individual users. The constant $c_2$ may serve as an offset parameter that adjusts the baseline level of the focus score, while $c_1$ may function as a scaling factor that determines the sensitivity of the normalized metric to changes in the underlying canonical correlation values. The normalization approach may help standardize the attention metric across different EEG signal amplitudes, stimulus intensities, and individual physiological variations that could affect the absolute magnitude of correlation coefficients.

The canonical correlation analysis may be implemented using numerical algorithms that efficiently solve the eigenvalue problems associated with the correlation maximization process. The computational implementation may employ singular value decomposition, QR factorization, or other matrix decomposition techniques that provide stable and accurate solutions even when the EEG data matrices exhibit rank deficiency or numerical conditioning issues. The algorithm selection may consider computational efficiency requirements for real-time processing as well as numerical stability considerations that ensure reliable correlation coefficient estimation across varying signal conditions.

In some embodiments, the processor applies regularization during canonical correlation analysis to improve numerical stability and generalization, for example when a dimensionality of an EEG data matrix is large relative to a number of samples available in a time window or epoch. Regularization may include ridge-regularized covariance estimation, shrinkage estimators, dimensionality reduction (e.g., principal component analysis) applied to EEG features and/or stimulus parameters before CCA, and/or constraints on projection vectors. Regularization parameters may be selected using cross-validation on stored data, predetermined defaults, and/or adaptive selection based on observed signal quality and matrix conditioning.

In some embodiments, the processor performs quality control for attention-metric computation to identify epochs or windows in which correlation estimates are unreliable (e.g., due to noise, motion artifacts, insufficient samples, or poor electrode contact). The quality control may include evaluating statistical significance of an estimated correlation, monitoring conditioning or rank of covariance matrices, and/or testing stability of computed projection vectors across data subsets. Epochs/windows failing quality criteria may be excluded from attention-metric aggregation and/or assigned reduced weights in subsequent adaptation of auditory stimulus parameters.

In some embodiments, the processor performs quality control for attention-metric computation to identify epochs or windows in which correlation estimates are unreliable (e.g., due to noise, motion artifacts, insufficient samples, or poor electrode contact). The quality control may include evaluating statistical significance of an estimated correlation, monitoring conditioning or rank of covariance matrices, and/or testing stability of computed projection vectors across data subsets. Epochs/windows failing quality criteria may be excluded from attention-metric aggregation and/or assigned reduced weights in subsequent adaptation of auditory stimulus parameters.

In some embodiments, the processor compares the attention metric to one or more thresholds to determine whether neural entrainment is sufficient for a current set of auditory stimulus parameters and whether parameter modification is warranted. Thresholds may be established from population statistics and/or individualized through calibration and may be fixed or adaptively adjusted over time. In some embodiments, the processor applies multi-criteria decision logic that considers an absolute attention-metric value, a change relative to a baseline or prior epochs, and/or temporal stability of the attention metric across consecutive windows. When the attention metric indicates insufficient entrainment (e.g., falls below a threshold), the processor initiates modification of one or more auditory stimulus parameters for delivery of a subsequent stimulus. In some embodiments, an upper threshold is additionally used to identify excessive entrainment and to reduce or suspend stimulation to mitigate sleep disruption.

In some embodiments, the processor modifies a stimulus frequency parameter using an iterative bounded update rule. For example, the processor updates a frequency value according to $f_{n+1}=f_n+\Delta f$, where $\Delta f$ is constrained to a predetermined bounded step size (and the frequency is optionally constrained to a predetermined allowable range). The processor may determine an adjustment direction based on changes in the attention metric across successive evaluations and may reverse a sign of $\Delta f$ when a subsequent attention metric decreases relative to a previous attention metric (e.g., when $a_k<a_{k-1}$}), thereby performing a hill-climb style search toward frequency settings that increase neural entrainment.

In some embodiments, the processor additionally or alternatively updates other auditory stimulus parameters, including amplitude/intensity and timing/phase. For example, an amplitude parameter may be updated according to $A_{n+1}=A_n+\Delta A$, with $\Delta A$ bounded and with an intensity parameter constrained by a maximum intensity threshold to reduce sleep disruption. Timing and/or phase may be adjusted by modifying a stimulus onset time relative to a detected phase of a slow-wave EEG component (e.g., a 0.5-4 Hz oscillation) so that subsequent stimuli occur within a predetermined phase window; in some embodiments, the phase adjustment is expressed as an update of a phase offset $\Phi$ by a bounded step size $\Delta\Phi$ over a cycle.

In some embodiments, the processor applies adaptive step-size control in which magnitudes of parameter changes are decreased when the attention metric is highly sensitive to changes and increased when responsiveness is low, to improve stability and convergence. The processor may employ multi-parameter optimization by jointly adjusting two or more parameters (e.g., frequency, amplitude, and onset timing/phase) according to an optimization policy that accounts for interactions among parameters; optionally, the policy may incorporate momentum terms based on prior adjustment directions to reduce oscillation. The processor may detect convergence or stabilization (e.g., based on attention-metric stability over multiple epochs or on diminishing parameter updates) and reduce a rate of parameter modification while maintaining parameter values that produce sustained entrainment.

In some embodiments, the processor reduces stimulation when the attention metric exceeds an upper criterion (e.g., to mitigate sleep disruption), including decreasing intensity, reducing deviations from a detected slow-wave rhythm, and/or introducing intermittent stimulation. The threshold comparison and parameter modification operations may be repeated during the sleep period to provide continuous closed-loop adaptation of auditory stimulation in response to changes in sleep depth, neural oscillation characteristics, and signal quality.

In some embodiments, the system is configured to compute, after completion of a sleep session, a sleep enhancement assessment that quantifies whether slow-wave sleep (SWS) was improved when the user slept while using the earbud device. During the sleep period, the earbud device continuously acquires EEG signals and the processor detects neural activity patterns indicative of deep sleep, including slow waves in a delta band (e.g., about 0.5-4 Hz). The processor stores or logs epoch-level and/or event-level measures derived from the continuous EEG, including at least a number of detected slow-wave events, amplitudes of the detected slow waves, and durations of classified slow-wave sleep stages. After the sleep session ends (e.g., when monitoring is terminated or an end-of-sleep condition is detected), the system aggregates these measures to compute a composite sleep-depth score for the session.

The composite sleep-depth score may be computed by comparing the session measures against user-specific baseline or threshold values obtained from historical sleep data for the same user, such as prior nights recorded without stimulation, prior sessions using the device, or both. For example, the system may determine a baseline deep-sleep duration for the user and evaluate whether the session deep-sleep duration, slow-wave count, and slow-wave amplitude exceed the baseline by at least predetermined margins or satisfy improvement criteria. In this manner, the composite sleep-depth score functions as an outcome metric indicating whether the adaptive auditory stimulation enhanced slow-wave sleep relative to the user's historical profile, and the score (or a derived enhancement indicator) may be stored in association with the session and optionally presented via a user interface as evidence of sleep enhancement and for longitudinal tracking.

By way of example, the system may determine that, when the user sleeps without stimulation, the user typically enters slow-wave sleep after a first latency interval and accumulates a baseline amount of deep sleep during a fixed sleep opportunity. During a subsequent session in which the user wears the earbud device, the system may detect, from the continuously received EEG signals, that the user transitions into slow-wave sleep earlier than the baseline (i.e., reduced slow-wave sleep latency) and remains in slow-wave sleep for longer durations (i.e., increased slow-wave sleep retention). In one practical recording scenario, the system classified approximately 2 hours of deep sleep within a 3-hour sleep interval, indicating both faster entry into slow-wave sleep and sustained slow-wave sleep once achieved. The system may reflect this improvement in the composite sleep-depth score by increasing a duration term (longer slow-wave stage time), and optionally increasing event-rate and amplitude terms (more and/or larger slow waves), relative to the user's stored baseline profile.

In some embodiments, the processor performs a causation analysis procedure to distinguish a stimulus-driven neural effect from spurious correlations that may arise due to coincidental timing or confounding factors. The causation analysis may be implemented as a perturbation test in which the processor establishes a baseline period during which the attention metric indicates stable entrainment, logs baseline stimulus parameters and EEG-derived slow-wave measures (e.g., dominant slow-wave frequency, delta-band power distribution, slow-wave event timing), and then deliberately perturbs one or more auditory stimulus parameters while monitoring for corresponding, predictable changes in slow-wave morphology.

In some embodiments, the perturbation test comprises controlled shifts of a stimulus-frequency parameter while maintaining one or more other parameters substantially constant (e.g., intensity and envelope shape), thereby isolating a causal contribution of frequency. The processor may apply bounded frequency offsets relative to a baseline value (optionally in both positive and negative directions) using gradual transitions and a hold interval sufficient to allow a neural response to stabilize, while enforcing sleep-safety constraints (e.g., intensity limits and arousal gating). During the perturbation intervals, the processor performs time-frequency and/or spectral analysis of the EEG signals to detect whether the slow-wave characteristics track the applied stimulus shifts, including estimating (i) a direction and magnitude of a neural frequency shift, and (ii) a response latency between the stimulus change and the detectable neural change.

In some embodiments, the processor evaluates causal influence using predefined criteria, including whether neural changes occur within a predetermined time window following the perturbation, whether the direction of the neural change corresponds to the direction of the stimulus shift, and whether the magnitude exceeds baseline variability. The processor may apply statistical testing by comparing perturbation intervals to control intervals in which no parameter change is applied, and may repeat multiple perturbation cycles to increase confidence. When causal influence is confirmed, the processor may increase confidence in subsequent parameter updates (e.g., allow larger bounded step sizes or reduce exploration time); when causal influence is not confirmed, the processor may reduce update aggressiveness, explore alternative stimulus parameters, or temporarily suspend adaptive updates while continuing safe stimulation. The causation protocol parameters (e.g., perturbation magnitude, timing, and repetition) may be personalized based on user characteristics, sleep stage, and historical responses, and results may optionally be stored to bias future optimization and/or learning-based parameter selection.

In some embodiments, results of a causation analysis are used to control aggressiveness of adaptive parameter updates. When the causation analysis indicates that controlled perturbations of a stimulus parameter (e.g., frequency shifts) produce corresponding and predictable changes in slow-wave morphology, the processor increases confidence in the closed-loop model and may reduce exploration time and/or allow more assertive bounded updates. Conversely, when the causation analysis does not demonstrate a consistent stimulus-driven response, the processor may treat the association as weak or spurious and may switch to alternative adjustment strategies (e.g., modifying a different parameter, changing stimulus type), reduce update aggressiveness, or temporarily suspend adaptive updates while maintaining safe baseline stimulation. In some embodiments, the causation protocol and its decision thresholds are personalized based on user characteristics, sleep stage, and historical responses, and safety monitoring (e.g., sleep-stage stability, micro-arousal detection, and intensity limits) is applied during causation testing to reduce sleep disruption; optionally, causation outcomes are stored and used to weight future parameter selections in learning-based optimization.

In some embodiments, the processor determines an instantaneous phase of a dominant slow-wave component of the EEG signals to coordinate stimulus timing with ongoing slow-wave oscillations. The processor may identify a dominant delta component within approximately 0.5-4 Hz by filtering and/or spectral analysis and compute instantaneous phase using an analytic-signal approach, for example by applying a Hilbert transform to a filtered delta-band signal and determining phase as an argument of the resulting complex-valued analytic signal (e.g., phase values in a 0 to $2\pi$ range). The processor may apply temporal smoothing and/or signal-quality checks to reduce phase jitter due to noise and artifacts.

In some embodiments, the processor uses a previously determined optimal lag $T_k$ (e.g., obtained from a lag sweep in canonical correlation analysis) to compensate for response latency and to time-shift an audio envelope or stimulus schedule used for subsequent stimulus delivery. For example, the processor predicts a time at which a target phase window will occur and schedules a burst onset and/or a peak of a stimulus envelope to occur within the target phase window, optionally after applying the lag-based time shift. In some embodiments, latency compensation additionally accounts for processing and delivery delays (e.g., sensing, computation, wireless transport, and audio rendering) using a predictive filter (e.g., a Kalman filter or other state-space predictor) that forecasts future phase based on recent phase/frequency estimates and updates latency estimates based on observed timing performance.

In some embodiments, phase-locked stimulus generation is performed in real time, including synthesizing noise bursts, tones, or modulated waveforms with controlled envelopes such that a defined temporal feature (e.g., stimulus onset or maximum envelope amplitude) is aligned to the target phase window. The processor may monitor achieved phase relationships (e.g., via phase coherence or circular correlation measures) and adapt a target phase window over time based on observed entrainment effectiveness for a particular user.

In some embodiments, the processor computes cross-frequency coupling (CFC) measures that quantify interactions between delta-band activity and one or more higher-frequency bands and uses the CFC measures to guide stimulus adaptation. The CFC measures may include phase-amplitude coupling (e.g., modulation of higher-frequency amplitude by delta phase), phase-phase coupling (e.g., phase-locking measures), and/or amplitude-amplitude coupling (e.g., correlation of bandpower envelopes), computed over sliding windows throughout the sleep period. The processor may apply statistical validation (e.g., surrogate/permutation testing) and/or quality gating to distinguish reliable coupling from artifacts.

In some embodiments, the processor combines the attention metric with one or more CFC measures to form a composite entrainment objective used for parameter updates. For example, when the attention metric exceeds a predetermined threshold indicating effective entrainment, the processor may modify the auditory stimulus to reinforce observed coupling (e.g., by adjusting modulation depth, selecting a waveform family, or altering spectral content) while maintaining safety bounds and sleep-stage gating. In some embodiments, coupling-guided adjustments are conditioned on context (e.g., deep sleep stability and absence of micro-arousals), and historical coupling profiles are stored to personalize future stimulus selection; optionally, learning-based models are trained to map coupling patterns and attention metrics to parameter-update actions.

In some embodiments, the processor modifies auditory stimulus parameters using an optimization policy that seeks to increase the attention metric (or another correlation-derived objective) subject to safety and sleep-maintenance constraints. The processor may estimate sensitivity of the objective to individual parameters by computing finite-difference approximations: for a current parameter vector p, the processor evaluates an objective value C(p), perturbs a selected parameter pi by a bounded increment Si while holding other parameters substantially constant, evaluates C(p+δi ei), and estimates a partial derivative as $$\frac{\partial C}{\partial p_i} \approx \frac{C(p+\delta_i e_i)-C(p)}{\delta_i}.$$

The resulting gradient vector ∇C(p) may be normalized to account for differing parameter scales (e.g., frequency vs. intensity vs. timing), and gradient magnitudes may be used to rank parameters for targeted adjustment and/or to hold low-sensitivity parameters substantially constant while optimizing higher-sensitivity parameters.

In some embodiments, the processor updates parameters iteratively according to $p_{n+1}=p_n+\alpha\nabla C(p_n)$ (or another gradient-directed rule), where a is a step size that may be fixed or adaptively adjusted based on convergence behavior and stability. Parameter updates may be constrained by bounded step sizes and allowable ranges, including (i) an intensity parameter bounded by a maximum intensity threshold and/or an individualized arousal threshold, (ii) timing constraints that place stimulus onset within a predetermined phase window of a 0.5-4 Hz EEG component, and (iii) frequency bounds within a predetermined range. Constraint handling may be implemented using projection (clipping), penalty terms, barrier functions, or other constrained-optimization techniques. The processor may also apply regularization that discourages abrupt parameter changes (e.g., penalties on large updates or rapid variations) and may detect convergence based on reduced gradient magnitude and/or stabilization of the attention metric, thereby reducing a frequency of parameter modifications once a stable configuration is reached.

In some embodiments, the optimization policy includes additional techniques such as momentum terms, multi-objective optimization that balances entrainment with sleep-stage stability and arousal risk, second-order or quasi-Newton updates, stochastic exploration, and/or parallel evaluation of multiple candidate parameter sets, with selection of a parameter set based on measured attention metrics and sleep-safety gating.

In some embodiments, the processor detects micro-arousal signatures in the EEG signals and adaptively adjusts an intensity parameter of the auditory stimulus to reduce sleep disruption while maintaining neural entrainment. Arousal detection may be performed during and/or after stimulus delivery using short analysis windows and may include detecting increases in higher-frequency activity (e.g., alpha, beta, and/or gamma band power), changes in spectral composition relative to deep sleep baselines, and/or abrupt changes in signal magnitude (e.g., RMS amplitude, peak-to-peak amplitude, or related statistics). The processor may implement change-detection logic (e.g., thresholding, cumulative-sum or sequential testing, and/or trained classifiers) and may optionally require consistency across multiple EEG channels when available to reduce false positives due to localized artifacts.

In some embodiments, responsive to detecting a micro-arousal signature, the processor reduces stimulus intensity and/or volume using a smooth ramp to avoid abrupt acoustic transitions and may suspend stimulus delivery when arousal indicators exceed a predetermined criterion or persist beyond a predetermined duration. The processor may apply hysteresis and/or minimum-hold times to prevent rapid oscillation between volume levels and may resume or restore intensity only after detecting restoration of stable slow-wave activity (e.g., sustained delta-band dominance and/or stable slow-oscillation measures) for at least a minimum stability period. The intensity parameter may remain bounded by a maximum intensity threshold, and the processor may terminate stimulation upon detecting wake state or non-deep sleep state.

In some embodiments, arousal-prevention control is coordinated with other adaptive parameter updates such that frequency/phase/waveform optimization is paused or down-weighted while arousal mitigation is active, thereby avoiding confounded updates during unstable sleep periods. Thresholds and response profiles for arousal detection and volume modulation may be user-specific and may be adapted over time based on observed tolerance and sleep stability.

In some embodiments, the system receives physiological data from at least one wearable device and uses the physiological data in combination with EEG signals to determine sleep state and/or to select initial stimulation settings. For example, the system may evaluate parasympathetic activation metrics measured prior to sleep onset, including heart rate variability (HRV) measures, to estimate user responsiveness to auditory stimulation and to adjust conservativeness of intensity limits, arousal thresholds, and/or initial stimulus parameters. HRV may be quantified using time-domain measures (e.g., SDNN and/or RMSSD) and/or frequency-domain measures (e.g., high-frequency power and/or LF/HF ratio), and the computed biomarker values may be stored in a user profile for personalization across sessions.

In some embodiments, the system receives physiological data from at least one wearable device and uses the physiological data in combination with EEG signals to determine sleep state and/or to adjust stimulation behavior. The wearable device may provide continuous or periodic measurements during a pre-sleep period and/or during sleep, including heart rate and heart rate variability (HRV), motion data (e.g., accelerometer-based restlessness), skin temperature, electrodermal activity, and/or respiratory measures. The processor may use the physiological data to estimate a pre-sleep autonomic state (e.g., parasympathetic activation level) and to predict responsiveness to auditory stimulation during subsequent slow-wave sleep, and may accordingly select initial stimulus parameters, adjust conservativeness of intensity limits and arousal thresholds, and/or gate initiation of stimulation.

In some embodiments, responsiveness prediction is performed using statistical models and/or trained machine-learning models that relate pre-sleep biomarker values (e.g., HRV measures such as SDNN, RMSSD, high-frequency power, and/or LF/HF ratio) to subsequent entrainment indicators such as attention metrics, slow-wave measures, and/or sleep-depth scores. The processor may improve robustness by interpreting HRV in view of motion context (e.g., discounting HRV intervals affected by movement), by using longitudinal data across multiple sessions to refine user-specific baselines, and/or by normalizing biomarker values for time-of-day or circadian factors. In some embodiments, the system applies safety gating such that stimulation aggressiveness is reduced or stimulation is deferred when the physiological data indicates high stress, excessive sympathetic activation, or other conditions associated with increased disruption risk.

In some embodiments, the processor performs an awake-state calibration to identify auditory stimuli and/or stimulus parameter ranges that maximize EEG synchronization for a particular user and stores resulting data as a personalized baseline for sleep-time stimulation. During calibration, the system presents a plurality of candidate auditory stimuli (e.g., noise bursts, rhythmic patterns, tones, and/or modulated waveforms) with controlled parameter variations (e.g., timing, tempo, intensity, spectral shaping, and modulation depth) while acquiring EEG signals from the earbud device. The processor computes one or more synchronization measures for each candidate stimulus, such as coherence, phase-locking, cross-correlation, and/or canonical correlation metrics (optionally using the same correlation pipeline used during sleep), and ranks or selects stimulus parameters that produce stronger and/or more reliable neural synchronization relative to a quiet baseline.

In some embodiments, the system stores the calibration results in a user profile, including selected stimulus types, initial parameter values, and individualized sensitivity information (e.g., an upper intensity limit or arousal-related tolerance estimate), and uses the stored profile to initialize sleep-time stimulation and reduce exploration time for closed-loop adaptation. The calibration protocol may optionally be repeated across sessions to update the stored baseline and to track stability of the user's response profile over time.

In some embodiments, the awake-state calibration is adaptive, such that the processor modifies a stimulus presentation protocol based on real-time neural response measurements to more efficiently explore a stimulus parameter space. For example, the processor presents candidate stimuli, computes synchronization metrics (e.g., coherence, phase-locking, cross-correlation, and/or canonical correlation values), and selects subsequent candidate parameter ranges based on observed metric improvements, thereby concentrating testing on parameter regions that are more likely to produce strong synchronization for the user. During calibration, the processor may perform quality control to ensure reliability of the measurements, including monitoring signal-to-noise ratio, detecting artifacts, and applying consistency checks across repeated presentations and/or channels; calibration measurements failing quality criteria may be discarded or down-weighted.

In some embodiments, the processor validates calibration usefulness by comparing calibration-derived predictions (e.g., selected initial parameter sets) to subsequent sleep-session effectiveness measures (e.g., attention metrics, slow-wave measures, and/or sleep-depth scores) and refines the calibration protocol based on observed prediction accuracy. The calibration baseline may be updated periodically (or upon detecting drift) to account for changes in user physiology or responsiveness over time, with updated baselines stored in a user profile for subsequent sessions. Optionally, population-level models may be used to provide initial parameter estimates for new users based on similarity of calibration responses to prior users, and the initial estimates may be refined by the user's own calibration data.

In some embodiments, the system analyzes historical EEG data and associated stimulation outcomes from multiple sleep sessions to predict effective auditory stimulus parameters for an individual user prior to or during a sleep session. The processor may extract features that characterize the user's slow-wave activity across nights (e.g., dominant delta frequency, delta-band power distributions, slow-wave regularity measures, phase-related features, and/or event-rate measures) using filtering and time-frequency analysis, and may pair such features with labels representing observed stimulation effectiveness (e.g., attention metrics, entrainment measures, and/or sleep-depth scores) and prior stimulus parameter values. A trained predictive model (e.g., a regression/classification model or neural network) may output recommended initial values and/or ranges for parameters such as stimulus frequency, intensity, and onset timing/ phase, subject to safety constraints (e.g., maximum intensity thresholds and arousal gating).

In some embodiments, the predicted parameters are used to initialize stimulation for a sleep session before applying closed-loop updates, thereby reducing exploration time and accelerating convergence to effective configurations. Optionally, the predictive model is updated over time using newly collected session data (e.g., online or incremental learning), and the model may additionally predict more complex temporal structures (e.g., envelope shape, inter-stimulus interval patterns, or rhythm variations) to support generation of personalized stimulus sequences.

In some embodiments, the processor generates the auditory stimulus in real time using a generative model conditioned on historical EEG data and current feedback metrics. For example, the processor inputs (i) a neural feature representation extracted from EEG signals (e.g., delta-band power, slow-oscillation phase/amplitude, event rate, or other embeddings), (ii) a current and/or recent attention metric value (and optionally a trajectory of attention metrics), and (iii) user profile data derived from prior sessions, and outputs a set of auditory stimulus parameters and/or a time-varying audio parameter matrix used to synthesize an auditory waveform for delivery by the earbud device.

In some embodiments, the generative model output is conditioned to maintain alignment with detected slow-wave activity, including selecting stimulus timing and envelope features to occur within a predetermined phase window of a 0.5-4 Hz EEG component and/or applying lag compensation (e.g., using an optimal lag value previously determined from correlation analysis). The output may include parameters such as onset times, pulse timing, amplitude envelope values, spectral shaping values, modulation rate/depth, and channel gains. Safety constraints may be enforced by post-processing and/or constrained decoding, including bounding an intensity parameter by a maximum intensity threshold, and reducing or suspending stimulation upon detecting micro-arousal signatures, wake state, non-deep sleep state, or poor signal quality.

In some embodiments, the processor updates the conditioning inputs and/or synthesis controls based on ongoing EEG monitoring and attention metric computation, such that the generated stimulus adapts across time windows during a sleep period. The system may apply audio quality checks (e.g., verifying amplitude limits, acceptable tempo/rate ranges, and permissible frequency-band emphasis) and may fall back to a predefined stimulus template (e.g., pink-noise bursts) when model output fails validation or when computational constraints prevent timely inference.

In some embodiments, the system maintains a library of previously used auditory stimulus parameter sets (or stimulus "templates") along with associated effectiveness measures (e.g., attention metrics, sleep-depth scores, and/or stability indicators) and selects candidate parameter sets for subsequent stimulation using an exploration/exploitation strategy. For example, the processor may implement a multi-armed bandit or contextual bandit policy that chooses between (i) exploiting high-performing parameter sets and (ii) exploring new or modified parameter sets, optionally conditioned on context such as sleep stage, time of night, or physiological state; selected parameter sets may then be further refined using the closed-loop correlation/attention-metric adaptation described herein.

In some embodiments, the processor applies time-decay weighting to historical performance data such that more recent sleep sessions contribute more strongly to parameter selection than older sessions. A temporal weighting function may be implemented using exponential decay, for example $w(t)=\exp(-\lambda t)$, where t is elapsed time since a session and $\lambda$ controls the decay rate; the processor may compute t using actual intervals between sessions (e.g., irregular spacing) and normalize weighted effectiveness measures to avoid bias due to varying session frequency. In some embodiments, lambda is adapted based on observed stability of responses (e.g., slower decay for stable users and faster decay when responsiveness drifts), and the processor uses the weighted data to rank or prioritize candidate stimulus parameter sets (including multi-parameter combinations) for initialization and/or subsequent adaptation, optionally validating stability using held-out sessions or cross-validation across historical windows.

In some embodiments, the processor applies time-decay weighting to historical performance data such that more recent sleep sessions contribute more strongly to parameter selection than older sessions. A temporal weighting function may be implemented using exponential decay, for example $w(t)=\exp(-\lambda t)$, where t is elapsed time since a session and $\lambda$ controls the decay rate; the processor may compute t using actual intervals between sessions (e.g., irregular spacing) and normalize weighted effectiveness measures to avoid bias due to varying session frequency. In some embodiments, $\lambda$ is adapted based on observed stability of responses (e.g., slower decay for stable users and faster decay when responsiveness drifts), and the processor uses the weighted data to rank or prioritize candidate stimulus parameter sets (including multi-parameter combinations) for initialization and/or subsequent adaptation, optionally validating stability using held-out sessions or cross-validation across historical windows.

In some embodiments, the processor computes a composite sleep-depth score used to gate initiation, continuation, or termination of auditory stimulation. The composite sleep-depth score may be computed from a plurality of slow-wave sleep indicators including (i) a number or rate of detected slow waves, (ii) an amplitude measure of the slow waves, and (iii) a duration of a slow-wave sleep stage (e.g., N3), where each indicator is derived from EEG analysis during a sleep period. In some embodiments, one or more indicators are normalized relative to an individual baseline derived from prior sessions without stimulation (or low-stimulation conditions) to enable comparison across users and nights, using robust statistics to reduce influence of outliers.

In some embodiments, the composite sleep-depth score is computed as a weighted combination of normalized indicators, for example $S=w_1M_{dur}+w_2M_{count}+w_3M_{amp}$, where $M_{dur}$, $M_{count}$, and $M_{amp}$ are normalized measures and $w_1$, $w_2$, and $w_3$ are coefficients selected to reflect desired tradeoffs between duration, event rate, and amplitude. The coefficients may be fixed, user-specific (e.g., learned from historical session outcomes), and/or constrained to maintain interpretability and stability.

In some embodiments, the processor uses the composite sleep-depth score to control stimulation state. For initiation, the processor may require the score to exceed an initiation threshold (optionally for a minimum stability period) before enabling stimulus delivery. During stimulation, the processor may continue delivery when the score remains within a target range and may modify parameters and/or suspend stimulation when the score decreases below a continuation threshold, indicates instability (e.g., increased arousal risk), or when the user transitions to wake or non-deep sleep state. The processor may terminate stimulation when the score indicates declining sleep depth, when a wake-time condition is met, or when signal quality is insufficient.

In some embodiments, gating thresholds are individualized and may be adapted over time based on user response patterns, time-of-night context, or longitudinal trends in the composite score, while enforcing safety bounds (e.g., maximum intensity limits and arousal gating). Optionally, the composite score and gating outcomes may be validated against independent sleep quality indicators (e.g., actigraphy or polysomnography when available) to adjust coefficients and thresholds.

In some embodiments, the processor segments EEG signals into epochs and classifies each epoch as stimulated or non-stimulated based on temporal overlap between an epoch interval and an audio-delivery interval. For example, the processor may compute an overlap measure (e.g., a duration or percentage of the epoch during which auditory stimulation is active) using synchronized timestamps for EEG acquisition and stimulus delivery, and may classify an epoch as stimulated when the overlap measure satisfies a predetermined overlap criterion and as non-stimulated when the overlap measure indicates no (or less than a threshold) overlap. In some embodiments, the processor applies quality control prior to classification and/or metric aggregation, including excluding or down-weighting epochs affected by artifacts, motion, or low signal quality.

In some embodiments, the processor computes attention metrics for epochs and compares stimulated versus non-stimulated conditions by computing a difference between a mean stimulated attention metric and a mean non-stimulated attention metric. A bootstrap resampling procedure may be applied to estimate a confidence interval for the difference by repeatedly sampling (with replacement) from the stimulated and non-stimulated epoch sets, computing a resampled mean-difference for each replicate, and deriving a percentile-based confidence interval. In some embodiments, the processor adjusts at least one auditory stimulus parameter when a lower bound of the confidence interval is greater than or equal to a predetermined margin.

In some embodiments, the processor additionally forms control intervals of matched duration from non-stimulated portions of a sleep session to compute empirical significance measures for observed stimulated-versus-control differences.

In some embodiments, the system generates for display on a graphical user interface: (i) a time-domain EEG trace, (ii) a power spectral density plot of EEG versus frequency, (iii) a band-power visualization for delta, theta, alpha, beta, and gamma bands, (iv) an audio waveform plot of the auditory stimulus versus time, (v) a time-frequency spectrogram for at least one of the EEG signals or the auditory stimulus, and (vi) an attention-metric trace, optionally time-aligned to stimulus delivery intervals and parameter updates.

In some embodiments, the graphical user interface includes a time-frequency spectrogram for at least one of the EEG signals or the auditory stimulus. The spectrogram may represent spectral magnitude or power over time and frequency, enabling assessment of frequency-specific neural activity and stimulus characteristics and their temporal relationships. In some embodiments, the interface presents an EEG spectrogram and an auditory-stimulus spectrogram using time-aligned axes to facilitate comparison between delivered acoustic content and corresponding neural responses.

In some embodiments, the interface is updated in real time (or near real time) as new EEG data, stimulus parameters, and derived metrics become available. The displayed information may include raw and/or filtered EEG traces, spectral measures, sleep stage classifications, the current auditory stimulus parameters (and/or an audio parameter matrix), and computed metrics such as attention metrics and sleep-depth scores, optionally synchronized to stimulus onset/offset events.

In some embodiments, the interface further provides signal-quality indicators (e.g., artifact flags or impedance measures), logging and export of session data and metrics, and configurable alerts when monitored metrics cross predetermined thresholds.

In some embodiments, the system includes a networked architecture in which a user device receives EEG data from an earbud device and provides control signals for auditory stimulus generation and delivery. Processing may be performed locally (e.g., on a smartphone or dedicated device), remotely (e.g., on a server), or in a distributed manner, provided that latency constraints support adaptive stimulus adjustment during a sleep period. The system may store session data and derived metrics for longitudinal tracking and personalization across sessions.

In one example, a user wears an earbud device during a sleep period, where the earbud device includes EEG electrodes positioned in the ear canal and one or more speakers for audio delivery. During the sleep period, the earbud device streams EEG signals to a processor (e.g., on a smartphone or a dedicated controller), which continuously preprocesses the EEG signals (e.g., filtering and artifact rejection) and segments the EEG signals into time windows/epochs for analysis. The processor monitors for a deep sleep state by detecting slow-wave activity, for example by identifying increased delta-band power in a 0.5-4 Hz band, slow-wave event rate, and slow-oscillation amplitude, optionally using a sliding-window decision logic to confirm stable deep sleep before intervention.

After deep sleep is confirmed, the processor causes delivery of an initial auditory stimulus using a current set of auditory stimulus parameters. For example, the stimulus comprises periodic pink-noise bursts having a defined burst duration and inter-burst interval, with a controlled amplitude envelope and bounded intensity to reduce arousal risk. During delivery, the processor logs stimulus parameters and forms an audio parameter matrix for the corresponding time window (e.g., a time-indexed matrix including burst onset markers, the amplitude envelope, and left/right channel gain values). In parallel, the processor extracts a neural feature representation from the EEG signals for the same time window (e.g., delta-band power over time, instantaneous slow-oscillation phase, and slow-wave event timing), and applies a correlation analysis algorithm to determine a correlation between the neural feature representation and the audio parameter matrix. From the correlation, the processor determines an attention metric that quantifies neural entrainment, such as a canonical correlation coefficient (optionally evaluated across candidate lag values and selected as a maximum correlation) or a phase-locking/coherence measure.

In this example, the attention metric initially remains below a threshold, indicating insufficient entrainment to the delivered stimulus. Responsive to the attention metric falling below the threshold, the processor modifies the auditory stimulus parameters and delivers a subsequent auditory stimulus. For instance, the processor first shifts a stimulus onset time to better align with a target phase window of the detected slow-wave oscillation and slightly adjusts an inter-burst interval (or modulation rate) within bounded step sizes while maintaining the intensity below a maximum threshold. The processor repeats the correlation computation on the subsequent window and determines that the attention metric increases but remains borderline; the processor then performs a second modification, such as incrementally adjusting the dominant stimulus tempo/frequency component (e.g., changing the burst repetition rate by a small step and reversing direction if the attention metric decreases) and/or changing the envelope shape (e.g., smoother attack/decay to reduce arousal risk while improving phase-locking). After these one or more adjustments, the processor observes that the attention metric rises above the threshold and remains stable across successive windows, indicating that neural entrainment has strengthened and the user is responding to the stimulation.

Once the attention metric indicates sufficient entrainment, the processor sustains the modified auditory stimulus parameters (optionally applying hysteresis to avoid rapid parameter toggling) and continues monitoring EEG for sleep continuity and signal quality. Over subsequent epochs, the EEG-derived slow-wave indicators show improvement relative to a pre-stimulation baseline, for example an increase in slow-oscillation amplitude and/or delta-band power, an increased slow-wave event rate, and an increased duration of time classified as deep sleep (e.g., extended N3 or slow-wave sleep segments). The processor may compute and update a sleep-depth score (e.g., combining slow-wave count, amplitude, and deep-sleep duration) to confirm that the intervention is beneficial, while also monitoring for micro-arousal signatures or motion artifacts; upon detecting arousal risk or degraded signal quality, the processor may reduce or suspend stimulation until stable deep sleep resumes.

The communication pathways illustrated in FIG. 1 may enable bidirectional data flow between earbud devices and processing systems, with neural activity measurements transmitted from the earbuds to the processors and stimulus control signals transmitted from the processors back to the audio delivery components within the earbuds. The network implementation may support various wireless communication protocols that enable reliable data transmission while minimizing power consumption to extend battery life during overnight monitoring sessions. The system architecture may incorporate edge computing capabilities where preliminary signal processing occurs locally on user devices before transmission to central processing systems, reducing network bandwidth requirements while enabling rapid response to critical events such as arousal detection or signal quality degradation.

Figure 2:
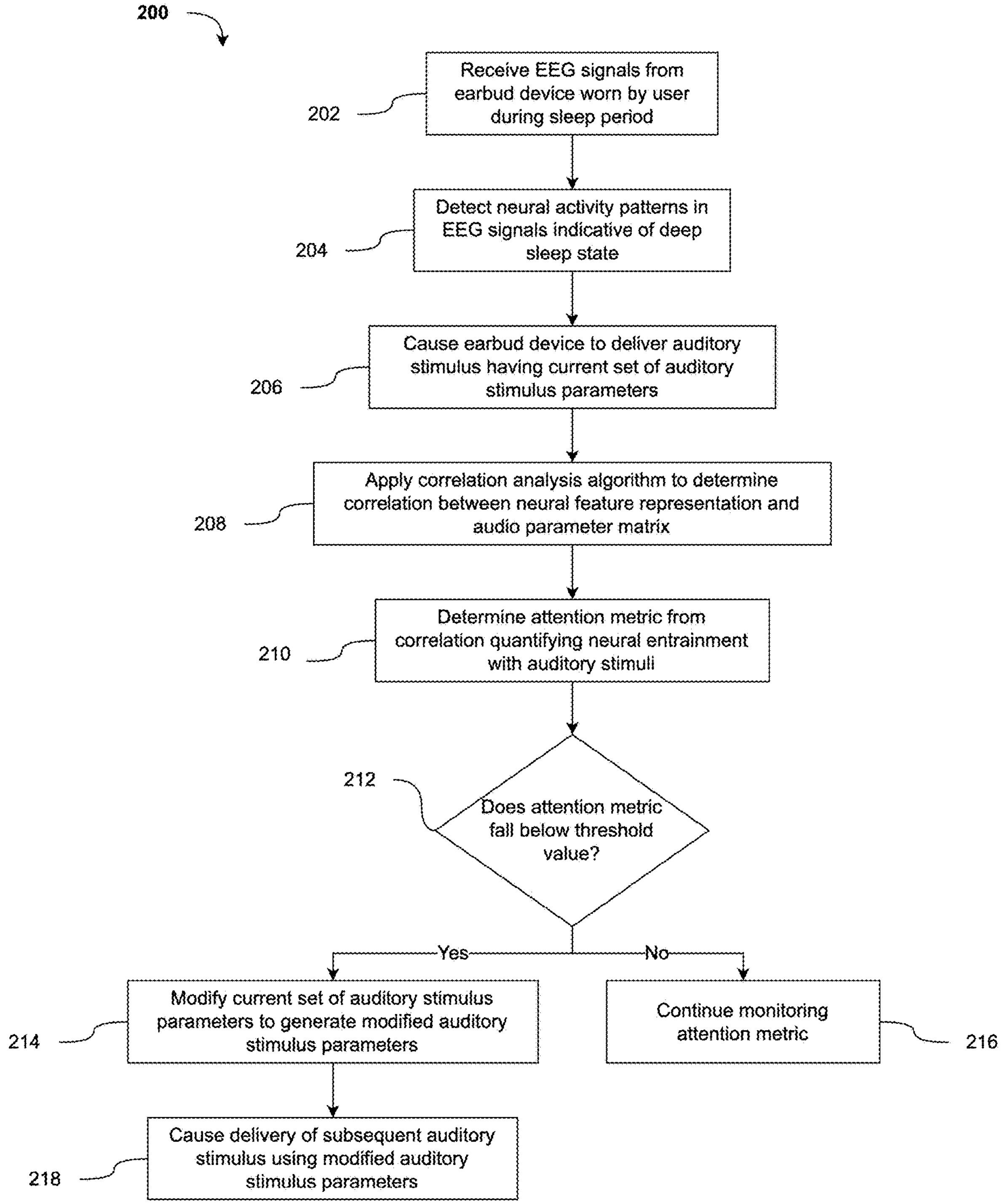
FIG. 2 illustrates a flowchart of a method for enhancing slow-wave sleep through adaptive auditory stimulation, according to aspects of the present disclosure.

FIG. 2 may illustrate a method flowchart that depicts the sequential steps involved in the basic adaptive auditory stimulation process. The method 200 may begin with step 202, where electroencephalogram signals are received from the earbud device during a sleep period, establishing the foundation for neural activity monitoring throughout the enhancement session. The method 200 may proceed to step 204, where neural activity patterns indicative of deep sleep states are detected through analysis of the received EEG signals, enabling identification of appropriate timing for auditory stimulus delivery. The detection process may involve spectral analysis of delta wave activity and evaluation of slow-wave characteristics that distinguish deep sleep from lighter sleep stages.

The method 200 may continue with step 206, where the earbud device is caused to deliver an auditory stimulus having a current set of parameters, initiating the acoustic intervention designed to enhance slow-wave oscillations. The stimulus delivery may be timed to coincide with detected slow-wave activity patterns to maximize the potential for neural entrainment. The method 200 may advance to step 208, where a correlation analysis algorithm is applied to determine relationships between neural feature representations extracted from the EEG signals and audio parameter matrices corresponding to the delivered stimuli. The correlation analysis may quantify the degree of synchronization between the acoustic input and the ongoing neural oscillations.

Step 210 of method 200 may involve determination of an attention metric from the computed correlation, providing a quantitative measure of neural entrainment effectiveness that guides subsequent parameter optimization decisions. The attention metric may represent the strength of the relationship between auditory stimuli and neural responses, with higher values indicating more effective synchronization. The method 200 may reach decision step 212, where the attention metric is compared to a predetermined threshold value to assess whether the current stimulus parameters are producing adequate neural entrainment. This decision point may determine whether parameter modifications are needed to improve stimulation effectiveness.

When the attention metric falls below the threshold value, the method 200 may proceed along the "Yes" branch to step 214, where the current set of auditory stimulus parameters is modified to generate new parameter configurations designed to enhance neural synchronization. The parameter modification process may involve adjustments to frequency, amplitude, phase, or other stimulus characteristics based on analysis of the neural response patterns. The method 200 may then continue to step 218, where delivery of a subsequent auditory stimulus using the modified parameters is initiated, implementing the adaptive optimization strategy. When the attention metric exceeds the threshold value, the method 200 may follow the "No" branch to step 216, where monitoring of the attention metric continues without parameter modification, maintaining effective stimulus configurations that are producing adequate neural entrainment.

Figure 3:
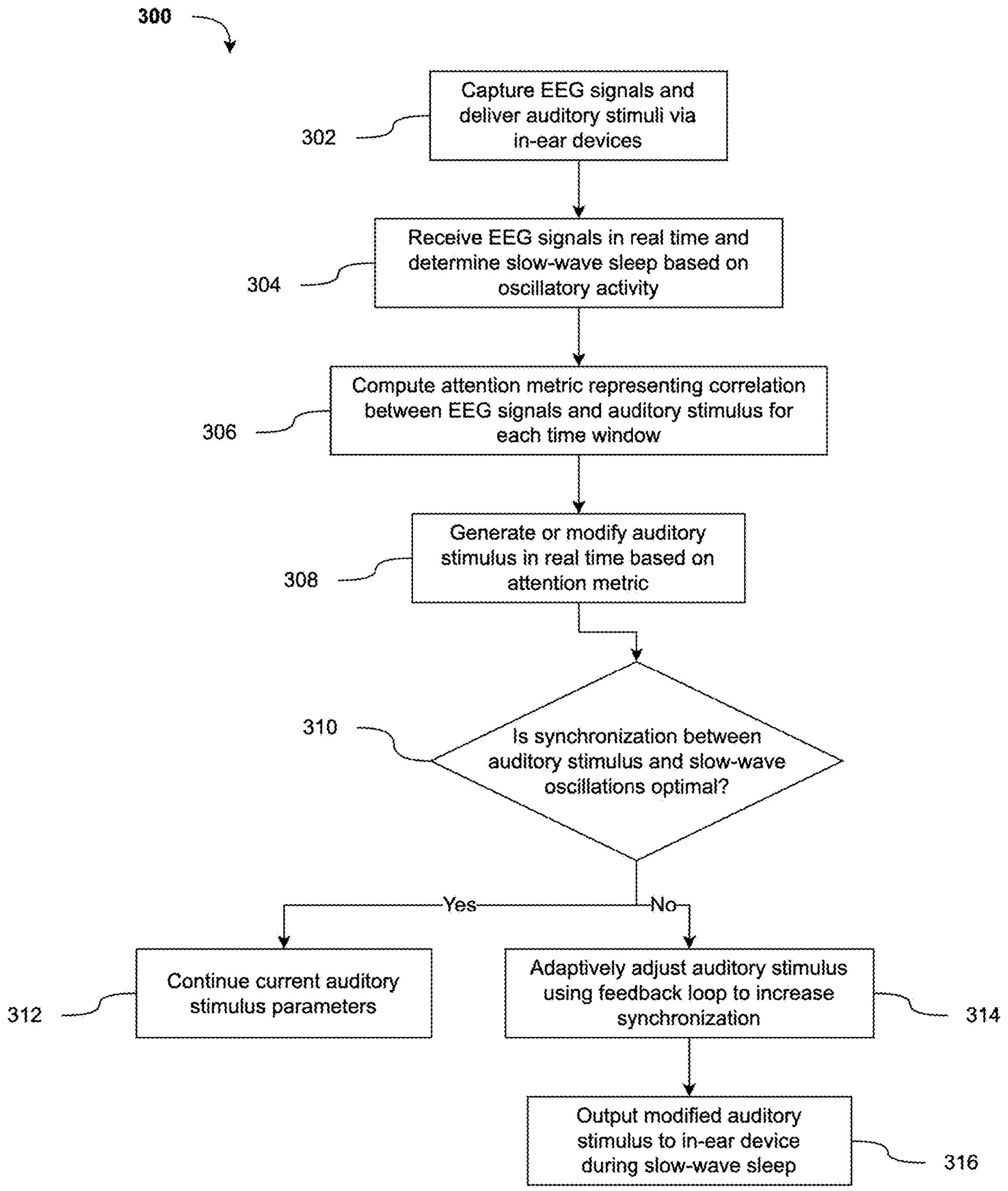
FIG. 3 illustrates a flowchart of a method for enhancing slow-wave sleep with real-time synchronization optimization, according to aspects of the present disclosure.

FIG. 3 may illustrate method 300, which depicts an enhanced adaptive stimulation approach that emphasizes real-time synchronization optimization. The method 300 may begin with step 302, where EEG signals are captured and auditory stimuli are delivered via in-ear devices, establishing the simultaneous monitoring and intervention capabilities that enable closed-loop optimization. The method 300 may proceed to step 304, where EEG signals are received in real time and slow-wave sleep is determined based on oscillatory activity characteristics, enabling continuous assessment of sleep state throughout the monitoring session.

Step 306 of method 300 may involve computation of an attention metric representing correlation between EEG signals and auditory stimulus for each time window, providing continuous quantitative feedback about neural entrainment effectiveness. The windowed analysis approach may enable tracking of synchronization changes over time while maintaining sufficient temporal resolution for responsive parameter adjustment. The method 300 may continue to step 308, where an auditory stimulus is generated or modified in real time based on the computed attention metric, implementing the adaptive feedback mechanism that optimizes neural entrainment.

The method 300 may reach decision step 310, which evaluates whether synchronization between auditory stimulus and slow-wave oscillations is optimal based on the attention metric and other neural response indicators. This decision point may determine whether the current stimulus configuration should be maintained or whether further optimization is needed. When synchronization is optimal, the method 300 may follow the "Yes" branch to step 312, where current auditory stimulus parameters are continued without modification, preserving effective entrainment conditions. When synchronization is not optimal, the method 300 may proceed along the "No" branch to step 314, where the auditory stimulus is adaptively adjusted using a feedback loop to increase synchronization, implementing systematic parameter modifications designed to improve neural entrainment effectiveness.

The method 300 may continue from step 314 to step 316, where the modified auditory stimulus is output to the in-ear device during slow-wave sleep, delivering the optimized acoustic intervention to the user. The continuous feedback loop structure illustrated in method 300 may enable ongoing optimization throughout the sleep period, with the system repeatedly evaluating synchronization effectiveness and adjusting parameters as needed to maintain optimal neural entrainment conditions.

Figure 4:
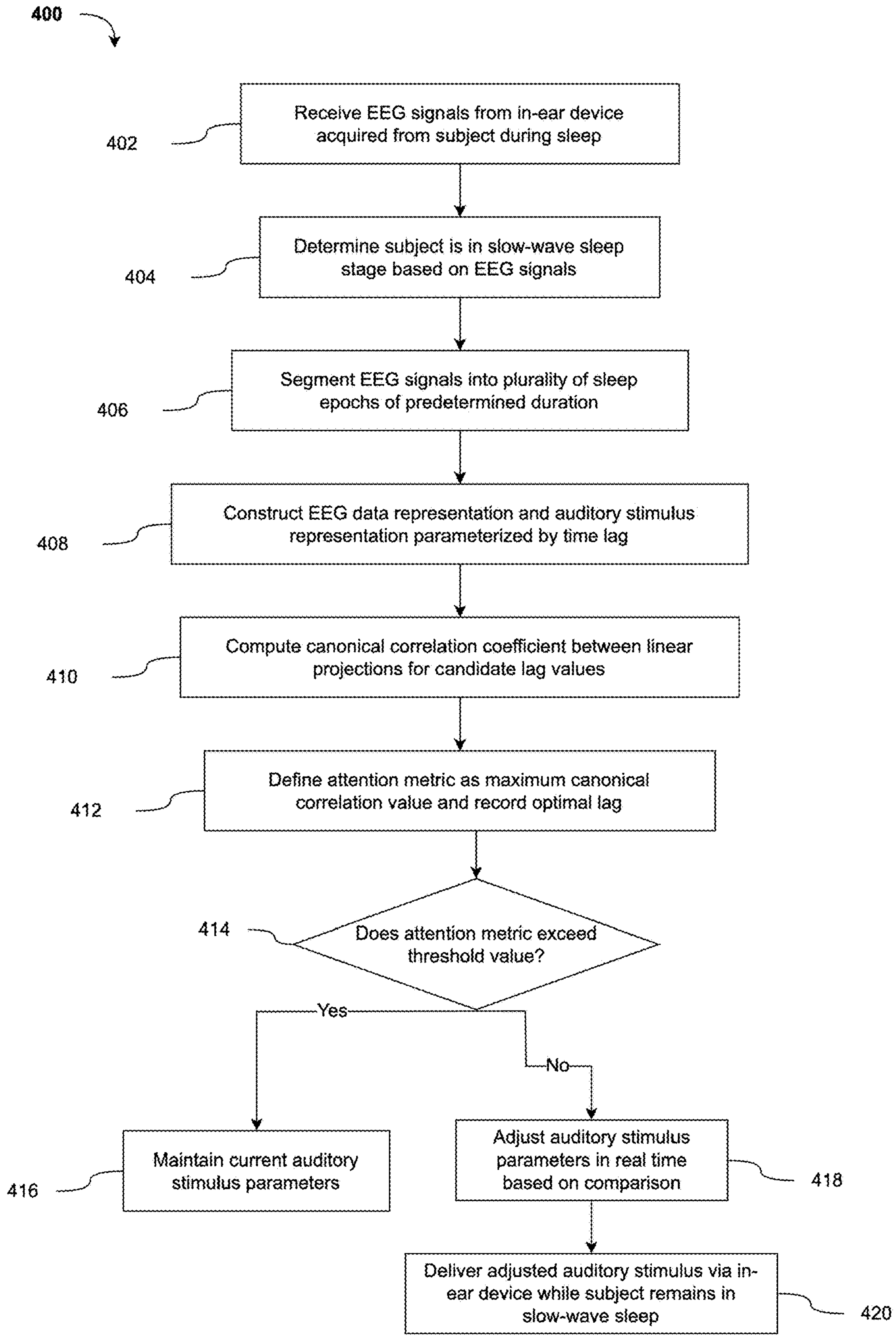
FIG. 4 illustrates a flowchart of a method for enhancing slow-wave sleep using canonical correlation analysis with lag optimization, according to aspects of the present disclosure.

FIG. 4 may illustrate method 400, which depicts a detailed implementation of canonical correlation analysis for neural entrainment assessment. The method 400 may begin with step 402, where EEG signals are received from an in-ear device acquired from a subject during sleep, establishing the data acquisition foundation for the correlation analysis approach. The method 400 may proceed to step 404, where the subject is determined to be in a slow-wave sleep stage based on the EEG signals, confirming appropriate conditions for auditory stimulation delivery.

Step 406 of method 400 may involve segmentation of the EEG signals into a plurality of sleep epochs of predetermined duration, creating discrete time windows that enable systematic correlation analysis across the sleep period. The epoch-based approach may provide standardized temporal units for computing attention metrics while enabling statistical comparison of stimulated and non-stimulated periods. The method 400 may continue to step 408, where an EEG data representation and an auditory stimulus representation parameterized by time lag are constructed, creating the mathematical structures needed for canonical correlation computation.

Step 410 of method 400 may involve computation of a canonical correlation coefficient between linear projections for candidate lag values, evaluating the strength of relationships between neural activity and auditory stimuli across different temporal offsets. The lag analysis may account for processing delays between stimulus delivery and neural response manifestation. The method 400 may proceed to step 412, where an attention metric is defined as a maximum canonical correlation value and an optimal lag is recorded, identifying both the strength of neural entrainment and the temporal relationship that produces maximum synchronization.

The method 400 may reach decision step 414, which determines whether the attention metric exceeds a threshold value, assessing whether current stimulus parameters are producing adequate neural entrainment. When the attention metric exceeds the threshold, the method 400 may follow the "Yes" branch to step 416, where current auditory stimulus parameters are maintained, preserving effective stimulation conditions. When the attention metric does not exceed the threshold, the method 400 may proceed along the "No" branch to step 418, where auditory stimulus parameters are adjusted in real time based on the comparison, implementing adaptive optimization to improve neural synchronization.

The method 400 may continue from step 418 to step 420, where the adjusted auditory stimulus is delivered via the in-ear device while the subject remains in slow-wave sleep, implementing the optimized stimulation protocol. The canonical correlation analysis approach illustrated in method 400 may provide mathematically rigorous assessment of neural entrainment while accounting for temporal relationships between stimuli and responses.

Figure 5:
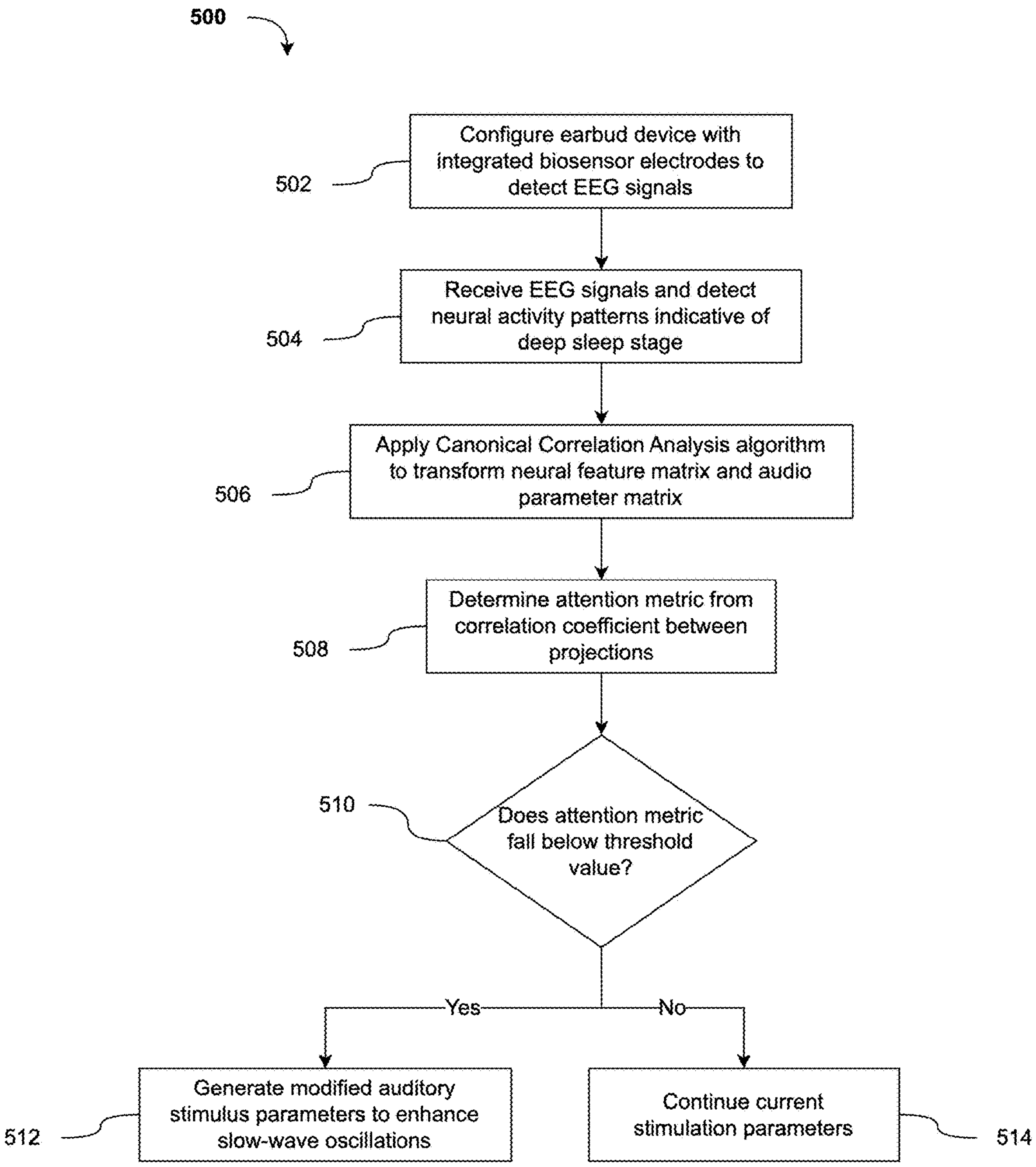
FIG. 5 illustrates a flowchart of a method for enhancing slow-wave sleep through canonical correlation analysis with integrated biosensor electrodes, according to aspects of the present disclosure.

FIG. 5 may illustrate method 500, which depicts an implementation approach that emphasizes the integration of biosensor electrodes within the earbud device configuration. The method 500 may begin with step 502, where an earbud device with integrated biosensor electrodes is configured to detect EEG signals, establishing the hardware foundation for neural activity monitoring. The integrated electrode approach may enable comfortable long-term wear during sleep while maintaining signal quality sufficient for correlation analysis.

The method 500 may proceed to step 504, which involves receiving EEG signals and detecting neural activity patterns indicative of a deep sleep stage, confirming appropriate conditions for auditory stimulation delivery. The method 500 may continue to step 506, where a canonical correlation analysis algorithm is applied to transform a neural feature matrix and an audio parameter matrix, computing the mathematical relationships between brain activity and acoustic stimuli. The transformation process may identify linear combinations of neural features and stimulus parameters that exhibit maximum correlation.

Step 508 of method 500 may involve determination of an attention metric from a correlation coefficient between projections generated in the previous step, quantifying neural entrainment effectiveness through the canonical correlation framework. The method 500 may reach decision step 510, which evaluates whether the attention metric falls below a threshold value, assessing the adequacy of current stimulation parameters. When the attention metric falls below the threshold, the method 500 may proceed along the "Yes" branch to step 512, where modified auditory stimulus parameters are generated to enhance slow-wave oscillations, implementing adaptive optimization. When the attention metric does not fall below the threshold, the method 500 may follow the "No" branch to step 514, where current stimulation parameters are continued without modification, maintaining effective neural entrainment conditions.

Figure 6A:
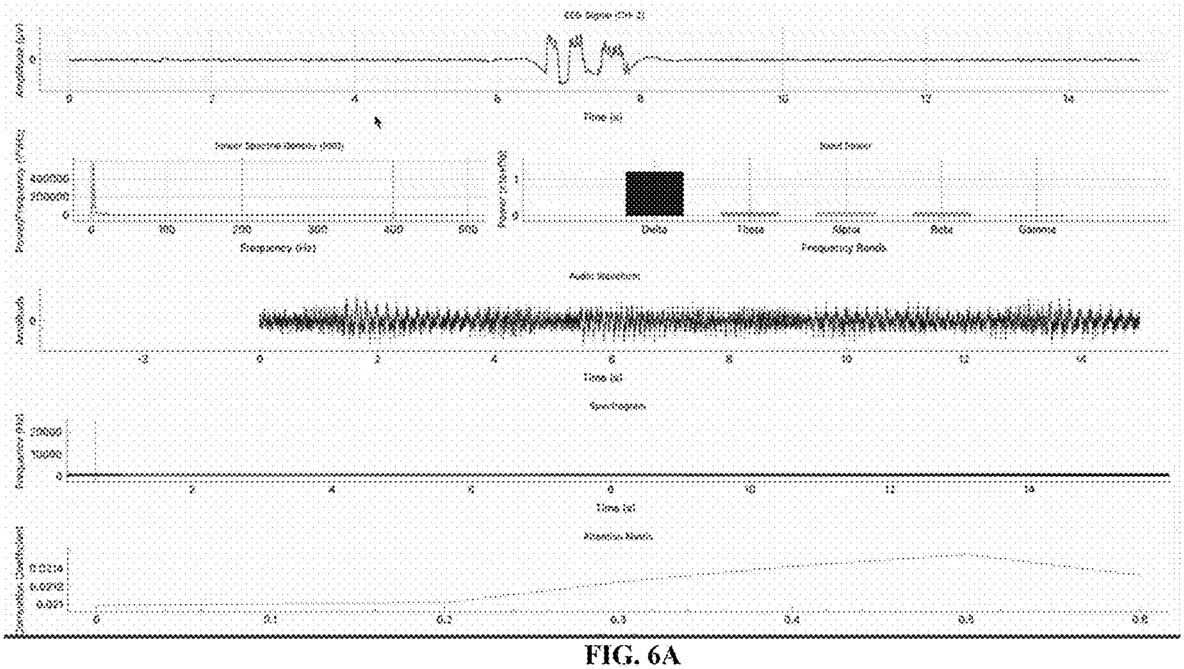
FIGS. 6A and 6B illustrates a graphical user interface for continuous display monitoring of EEG signals and auditory stimulation parameters, according to aspects of the present disclosure.
Figure 6B:
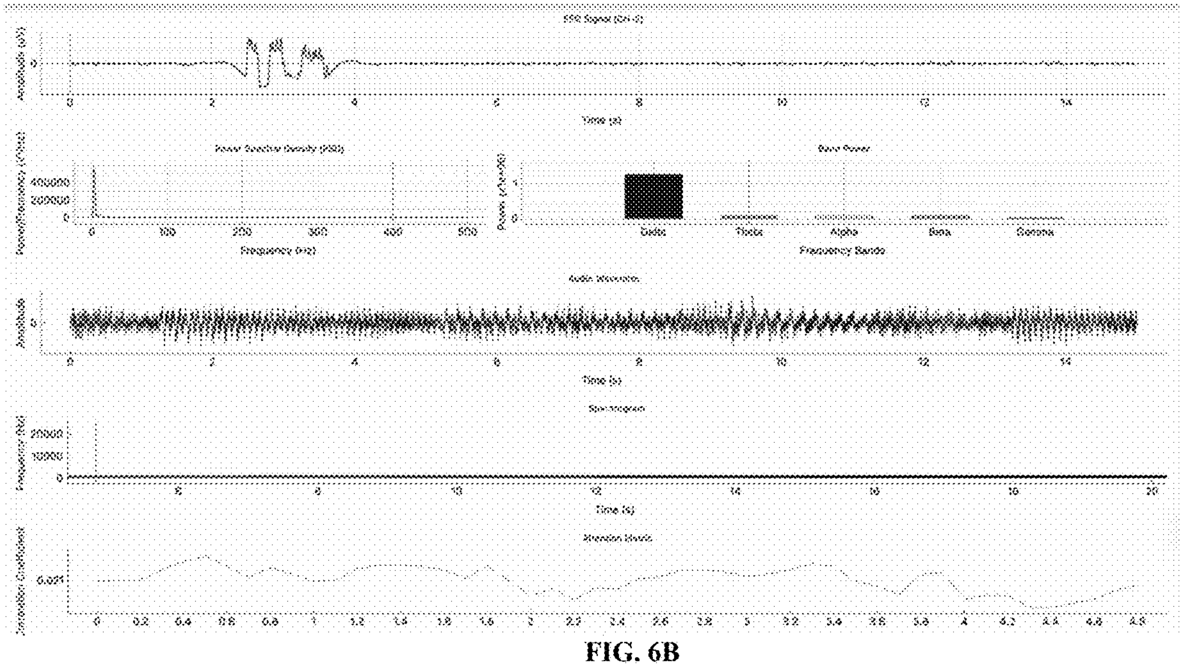

FIG. 6A and FIG. 6B illustrate example outputs generated by a processor during an adaptive auditory stimulation session in which EEG signals acquired from an earbud device are analyzed within a time window (or sleep epoch) associated with delivery of an auditory stimulus. In each of FIG. 6A and FIG. 6B, the upper panel shows an example EEG time-domain trace (e.g., Channel CH-2) for the time window, and one or more intermediate visualizations may include a power spectral density (PSD) plot and a band-power summary indicating relative power in a plurality of frequency bands (e.g., delta, theta, alpha, beta, and gamma), where delta dominance is indicative of a deep sleep state. Additional panels depict example auditory stimulus information for the same time window, including an audio waveform and a time-frequency spectrogram representing spectral content and/or temporal modulation of the delivered stimulus. The lower panel illustrates an example attention metric derived from a correlation analysis between (i) a neural feature representation extracted from the EEG signals for the time window and (ii) an audio parameter matrix corresponding to a current set of auditory stimulus parameters, where the attention metric quantifies neural entrainment to the delivered auditory stimulus. In some embodiments, the plotted attention metric represents a correlation coefficient (e.g., canonical correlation) evaluated across multiple candidate temporal lag values to account for response latency, and the processor may use the attention metric (and optionally an associated optimal lag) to determine whether to modify subsequent auditory stimulus parameters.

In some embodiments, the disclosed techniques are implemented as a closed-loop neurostimulation control system that operates on physiological signals acquired from a physical EEG sensor integrated in an earbud device and that generates real-time control signals for driving an acoustic transducer in the same device.

The correlation analysis and attention metric are executed on time-synchronized EEG samples produced by electrodes in contact with ear tissue, and the resulting output is used to select, time, and parameterize subsequent auditory stimuli physically delivered to the user during sleep. Accordingly, the disclosed processing is tied to particular sensing and output hardware and produces a concrete, real-world effect in the form of controlled auditory stimulation and measured changes in neurophysiological activity.

The disclosed correlation analysis (including, in some implementations, canonical correlation over candidate lag values) is used as a computationally efficient feedback measure to compensate for system latency and neural response delay, thereby improving the timing accuracy of stimulation relative to ongoing slow-wave oscillations. By forming an EEG-derived neural feature representation and an audio parameter matrix for the same time window, and selecting an attention/entrainment metric that captures stimulus-response alignment, the system can automatically adjust stimulus parameters (e.g., onset timing/phase window, repetition rate, envelope, and bounded intensity) to maintain effective entrainment while avoiding arousal. This improves the functioning of the sleep-enhancement system itself (for example, but not limited to, reduced mistimed stimulation, improved stability of parameter updates, and more reliable entrainment detection under real-time constraints).

In addition, the disclosed system incorporates signal-quality gating and safety constraints that enable practical deployment in a wearable sleep environment. For example, the processor may suppress parameter modification during detected artifact conditions (e.g., motion/electrode disturbance) and may reduce or terminate stimulation upon detection of micro-arousal or non-deep sleep states, while maintaining stimulus intensity below a maximum threshold to reduce sleep disruption. These operational safeguards and hardware-coupled control actions demonstrate that the disclosed techniques provide a specific technological solution for real-time physiological monitoring and adaptive stimulation-improving robustness, safety, and effectiveness of earbud-based sleep neurostimulation.

A number of implementations have been described. Nevertheless, it will be understood that various modifications may be made without departing from the spirit and scope of the disclosure. Accordingly, other implementations are within the scope of the following claims.

The invention claimed is:

1. A method for enhancing slow-wave sleep through adaptive auditory stimulation, the method comprising:

continuously receiving, by a processor, electroencephalogram (EEG) signals from an earbud device configured to be worn by a user during a sleep period;

detecting, by the processor, neural activity patterns in the EEG signals indicative of a deep sleep state;

causing, by the processor, the earbud device to deliver to the user an auditory stimulus having a current set of auditory stimulus parameters;

applying, by the processor, a correlation analysis algorithm to determine, for a time window associated with the delivered auditory stimulus, a correlation between a neural feature representation extracted from the EEG signals and an audio parameter matrix corresponding to the current set of auditory stimulus parameters, wherein the neural feature representation comprises one or more numerical features extracted from the EEG signals, including at least one of a band power feature, a signal amplitude feature, a signal phase feature, and a slow-wave event feature;

determining, by the processor, an attention metric from the correlation, wherein the attention metric quantifies neural entrainment of the neural activity patterns and the auditory stimulus delivered to the user;

based on the attention metric falling below a threshold value for the attention metric, modifying, by the processor, the current set of auditory stimulus parameters to generate modified auditory stimulus parameters; and causing, by the processor, delivery of a subsequent auditory stimulus using the modified auditory stimulus parameters to enhance slow-wave oscillations associated with the deep sleep state in the user's brain during the sleep period.

2. The method of claim 1, wherein modifying the current set of auditory stimulus parameters comprises adjusting at least one of stimulus frequency, phase, amplitude, tempo, or waveform shape.

3. The method of claim 1, wherein the modified auditory stimulus parameters, while being used to deliver the subsequent auditory stimulus, cause at least one of maintaining or increasing the neural entrainment between the auditory stimulus and the neural activity patterns, as quantified by the attention metric.

4. The method of claim 1, comprising performing, by the processor, an awake-state calibration to identify auditory stimuli that maximize neural entrainment of the EEG signals, and storing resulting data as a personalized baseline for sleep-time stimulation.

5. The method of claim 1, wherein detecting the neural activity patterns in the EEG signals further comprises segmenting the EEG signals into a plurality of sleep epochs, each epoch having a predetermined duration.

6. The method of claim 5, further comprising classifying each epoch as stimulated or non-stimulated based on temporal overlap between the epoch and an audio-delivery interval.

7. The method of claim 6, further comprising:

computing a difference between a mean stimulated attention metric and a mean non-stimulated attention metric, applying a bootstrap resampling procedure to estimate a confidence interval for the difference, and using the confidence interval to determine whether to modify the current set of auditory stimulus parameters, and wherein the mean stimulated attention metric comprises a mean of attention metric values computed for epochs classified as stimulated, and wherein the mean non-stimulated attention metric comprises a mean of attention metric values computed for epochs classified as non-stimulated, and wherein modifying the current set of auditory stimulus parameters comprises adjusting at least one parameter of the auditory stimulus based on a lower bound of the confidence interval being greater than or equal to a predetermined margin.

8. The method of claim 1, wherein determining the correlation comprises performing canonical correlation analysis by the correlation analysis algorithm to compute a canonical correlation coefficient, for the time window associated with the delivered auditory stimulus, between a linear projection of an EEG data matrix and a linear projection of an audio parameter matrix corresponding to the current set of auditory stimulus parameters.

9. The method of claim 8, wherein the canonical correlation coefficient is computed for each of a plurality of candidate lag values each defining a respective temporal offset between the EEG data matrix and the audio parameter matrix, and wherein the attention metric comprises a maximum canonical correlation coefficient across the plurality of candidate lag values.

10. The method of claim 9, further comprising storing an optimal lag value associated with the maximum canonical correlation coefficient, and using the optimal lag value to time-shift a temporal envelope used to control timing of delivery of a subsequent auditory stimulus.

11. The method of claim 1, further comprising normalizing the attention metric to a bounded normalized value within a predetermined range.

12. The method of claim 1, wherein modifying the current set of auditory stimulus parameters comprises incrementally modifying a stimulus frequency by a bounded step size, and reversing a sign of the step size based on a subsequent attention metric decreasing relative to a previous attention metric.

13. The method of claim 1, further comprising computing cross-frequency coupling measures between delta band activity and at least one higher frequency band, and modifying the auditory stimulus to reinforce observed cross-frequency coupling based on the attention metric exceeding a predetermined threshold.

14. The method of claim 1, further comprising, based on the EEG signals received during the sleep period, computing a composite sleep-depth score based on a number of detected slow waves, an amplitude of the slow waves, and a duration of a slow-wave sleep stage, and determining sleep enhancement by comparing the composite sleep-depth score to a user-specific baseline derived from historical sleep-session data.

15. The method of claim 1, further comprising detecting micro-arousal signatures in the EEG signals, and disabling or reducing the auditory stimulus upon detecting the micro-arousal signatures.

16. The method of claim 1, further comprising generating the auditory stimulus in real-time using a generative model conditioned on historical EEG data and current attention metrics.

17. The method of claim 1, further comprising receiving physiological data from at least one wearable device, and using the physiological data in combination with the EEG signals to determine the deep sleep state.

18. The method of claim 1, wherein the attention metric comprises at least one of a phase-locking value, a coherence value, or a normalized cross-correlation value.

19. The method of claim 1, wherein the neural feature representation comprises at least one of delta-band power in a 0.5 to 4 Hertz (Hz) band, slow-oscillation phase, slow-oscillation amplitude, or slow-wave event rate.

20. The method of claim 1, wherein the audio parameter matrix comprises at least one of stimulus onset times, an amplitude envelope of the auditory stimulus, or a parameter vector including timing and intensity.

21. The method of claim 1, wherein modifying the current set of auditory stimulus parameters comprises adjusting a stimulus onset time to occur within a predetermined phase window of a 0.5 to 4 Hertz (Hz) component of the EEG signals.

22. The method of claim 1, further comprising detecting an artifact condition based on motion data from an accelerometer of the earbud device, and suppressing modification of the auditory stimulus parameters during the artifact condition.

23. The method of claim 1, wherein causing, by the processor, delivery of the auditory stimulus or the subsequent auditory stimulus comprises outputting one or more pink-noise bursts having a duration within a predetermined range.

24. The method of claim 1, wherein the auditory stimulus parameters include an intensity parameter bounded by a maximum intensity threshold to reduce sleep disruption.

25. The method of claim 1, further comprising terminating delivery of the subsequent auditory stimulus upon detecting a wake state or a non-deep sleep state.

26. The method of claim 1, wherein applying the correlation analysis algorithm comprises determining the correlation using at least one of Pearson correlation, Spearman rank correlation, mutual information, coherence, cross-correlation, or a correlation coefficient computed between respective projections of the neural feature representation and the audio parameter matrix.

27. The method of claim 26, wherein applying the correlation analysis algorithm comprises using a trained machine-learning model that outputs a correlation score indicative of association between the neural feature representation and the audio parameter matrix.

28. The method of claim 1, further comprising generating, for display on a graphical user interface, (i) a time-domain EEG trace, (ii) a power spectral density plot of the EEG signals versus frequency, (iii) a band-power visualization for delta, theta, alpha, beta, and gamma bands, (iv) an audio waveform plot of the auditory stimulus versus time, (v) a time-frequency spectrogram for at least one of the EEG signals or the auditory stimulus, and (vi) an attention-metric trace.

* * * * *